United States Patent
Ichida et al.

[11] Patent Number: 6,077,481
[45] Date of Patent: Jun. 20, 2000

[54] AUTOMATIC PRETREATMENT SYSTEM FOR ANALYZING COMPONENT OF SPECIMEN

[75] Inventors: Kaoru Ichida, Toyohashi; Yoshikatsu Mori; Takao Tozawa, both of Tokyo, all of Japan

[73] Assignee: Japan Tobacco, Inc., Tokyo, Japan

[21] Appl. No.: 09/052,006

[22] Filed: Mar. 31, 1998

[30] Foreign Application Priority Data

Mar. 31, 1997 [JP] Japan .................................. 9-080741
Nov. 14, 1997 [JP] Japan .................................. 9-313807

[51] Int. Cl.$^7$ ................................................ G01N 35/02
[52] U.S. Cl. ................................ 422/65; 422/63; 422/72; 436/43; 436/45; 436/47; 436/48; 436/49
[58] Field of Search ................................. 422/63, 65, 67, 422/81, 100, 102, 104, 72; 436/43, 45, 47, 48, 49, 54, 174, 179, 180

[56] References Cited

U.S. PATENT DOCUMENTS

| | | | |
|---|---|---|---|
| 3,628,405 | 12/1971 | Fleisher | 422/99 |
| 4,735,776 | 4/1988 | Yamamoto et al. | 422/65 |
| 4,982,553 | 1/1991 | Itoh | 53/246 |
| 5,340,544 | 8/1994 | Nishikawa et al. | 422/99 |
| 5,472,669 | 12/1995 | Miki et al. | 422/63 |
| 5,525,298 | 6/1996 | Anami | 422/63 |
| 5,551,828 | 9/1996 | Iles | 414/757 |
| 5,735,387 | 4/1998 | Polaniec et al. | 198/690.1 |
| 5,814,276 | 9/1998 | Riggs | 422/65 |

FOREIGN PATENT DOCUMENTS 0629858  12/1994  European Pat. Off. .

*Primary Examiner*—Long V. Le
*Attorney, Agent, or Firm*—Birch, Stewart, Kolasch, Birch, LLP

[57] ABSTRACT

The automatic pretreatment system for analyzing component of a specimen includes a pouring section for pouring a predetermined solvent into a distribution vial in which the specimen is accommodated, a shaking section for shaking the distribution vial after the solvent is poured, and a distribution section for distributing the specimen liquid in the distribution vial into one or more test vials after shaking. The sending and receiving of the vial between each of the sections, the supply of the test vial into the distribution section, and treatment in each of the sections are carried out automatically.

12 Claims, 18 Drawing Sheets

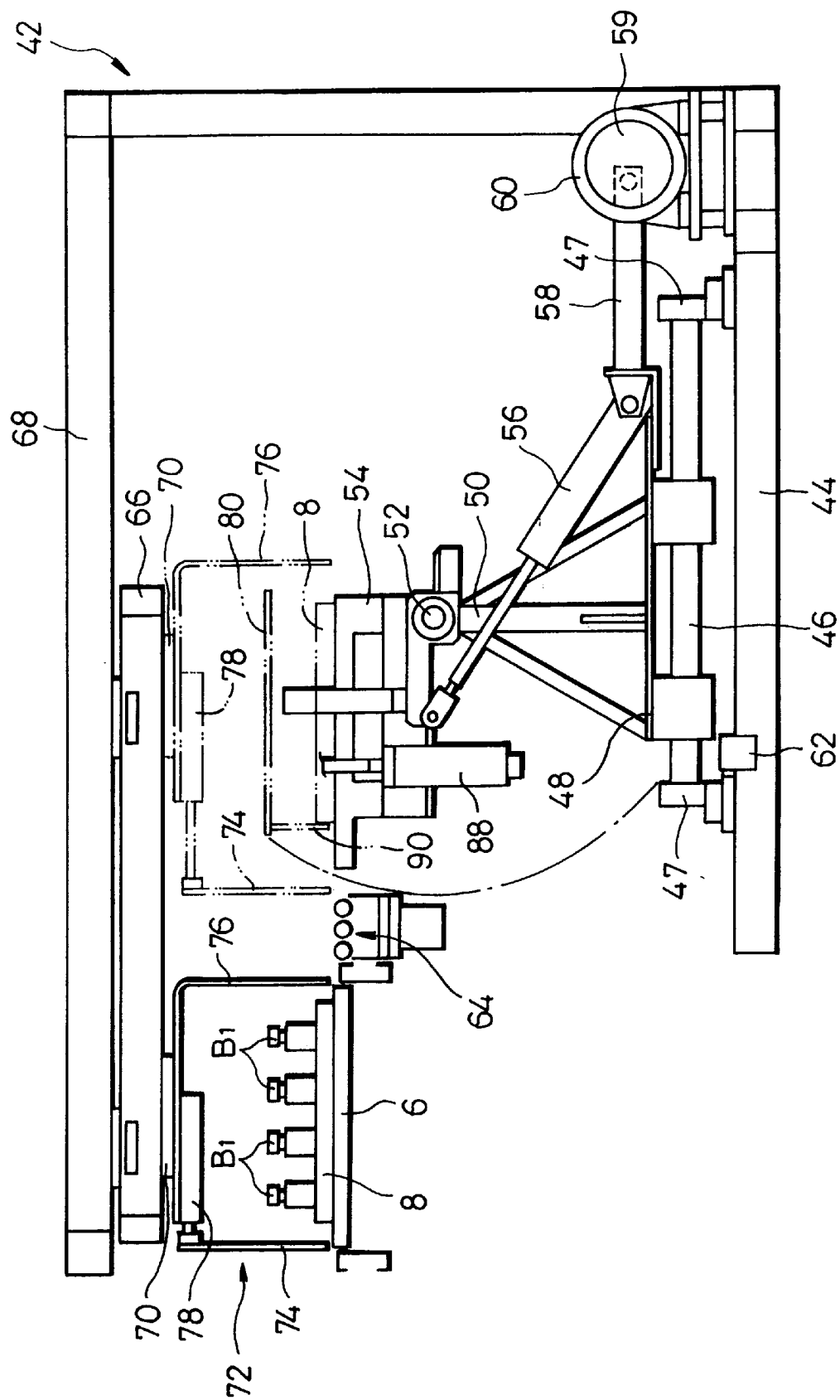

F I G. 7A
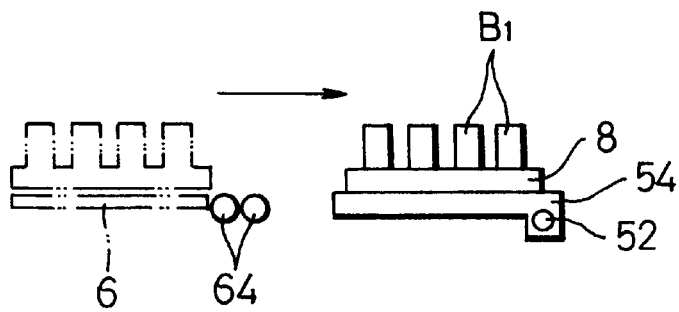
F I G. 7B
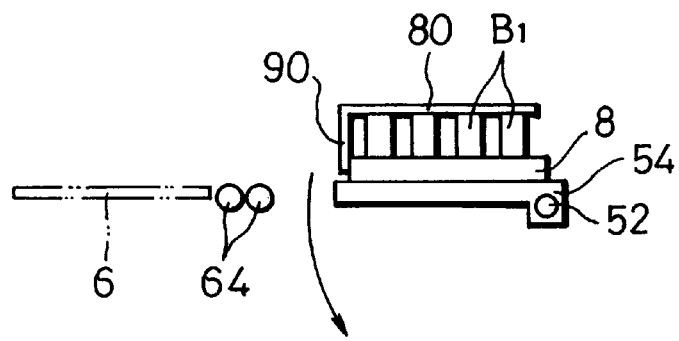
F I G. 7C
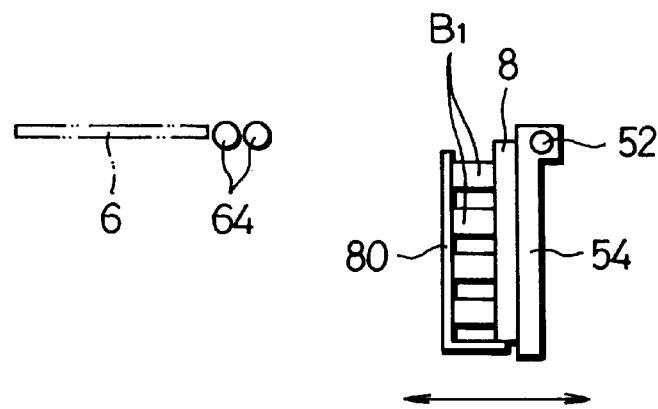

F I G. 23
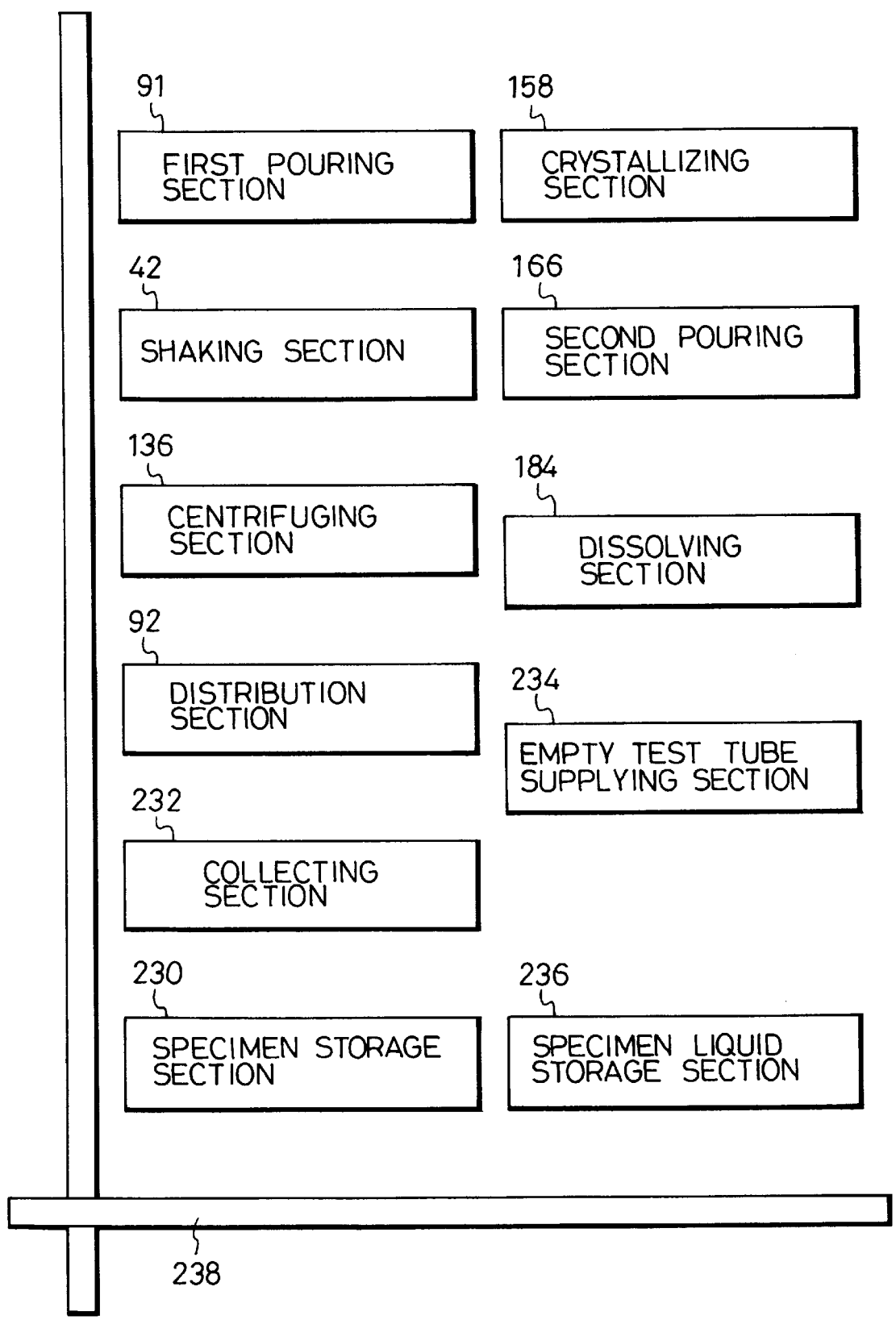

AUTOMATIC PRETREATMENT SYSTEM FOR ANALYZING COMPONENT OF SPECIMEN

BACKGROUND OF THE INVENTION

1. Field of the Invention

The present invention relates to a system for automatically pretreating a specimen prior to an analysis of components of the specimen in medicinal or chemical field and the like.

2. Description of the Related Art

Analysis of components of a specimen requires a pretreatment, and such pretreatment is carried out through the following procedural steps. First, a predetermined solvent is poured into a distribution vial in which a specimen is accommodated. The distribution vial is shaken for a predetermined time by a shaking apparatus. During the shaking time for the distribution vial, the component of the specimen is extracted into the solvent, and a specimen liquid is obtained. After shaking, the specimen liquid is separately poured into one or a plurality of test vials, and the pretreatment is completed. In some cases, the specimen liquid in the distribution vial may be subjected to a centrifuging treatment by a centrifugal separator.

When the pretreatment for an analysis is completed, the specimen liquid in the test vial is analyzed by analyzing apparatus such as gas chromatography or liquid chromatography.

The above described pretreatment of the specimen includes processes of: opening and closing of the cap or plug of a distribution vial or test vial, pouring a solvent into the distribution vial, loading and unloading of the distribution vial into and from a shaking apparatus or a centrifugal separator, and pouring the specimen liquid from a single distribution vial into a single or a plurality of test vials. Conventionally, all of these processes are carried out manually and thus, the pretreatment for the analysis requires a great labor. Further, one must pay the closest attention to handling of the distribution vial and the test vial in each of the processes and therefore, the performance of pretreatment operation of the specimen liquid is low.

SUMMARY OF THE INVENTION

It is an object of the present invention to provide a system for automatically pretreating a specimen which automates each the above described processes of the pretreatment, and which is capable of reducing manual labor.

The above object is achieved by an automatic pretreatment system of the present invention, and the pretreatment system comprises: a storage section for storing a vessel with cap or plug, the vessel containing a specimen; a pouring section for pouring a solvent for preparing a specimen liquid in the vessel, the pouring section including means for opening and closing the cap or plug of the vessel; a shaking section for shaking the vessel after the solvent is poured; and transfer means for sequentially transferring from the storage section to the pouring section and the shaking section.

According to the pretreatment system, since the pouring section includes the means for opening and closing the cap or plug of the vessel, the processes from the pouring of the solvent into the vessel to the shaking of the vessel can be automated.

The system further comprises: a second storage section for storing empty second vessels; a distribution section for receiving the first vessel transferred from the shaking section by means of the first transfer means and at least one second vessel transferred from the second storage section by means of second transfer means, and distributing the specimen liquid in the first vessel to the second vessel, the distribution section including means for opening and closing the cap or plug of the first vessel; a closing section for closing the second vessel with cap or plug after the specimen liquid is poured; and a receiving section for receiving the second vessel from the closing section.

In this case, after the first vessel is shaken, the distribution process of the specimen liquid from the first vessel to the second vessel, and the processes for the closing and the collection of the second vessel can be automated.

The pretreatment system may further include a centrifuging section. The centrifuging section centrifuges the specimen liquid in the first vessel after the first vessel is shaken. In this case, the distribution section may include a detector for detecting a boundary or interface between liquid layers separated in the specimen liquid in the first vessel.

Further, the pretreatment system may include sections for receiving the second vessel by means of the second transfer means and carrying out various processes with respect to the second vessel before the second vessel is transferred to the receiving section. These sections include a crystallizing section for crystallizing the specimen liquid in the second vessel; a second pouring section for pouring a second solvent into the second vessel after the crystallization, and a dissolving section for dissolving the crystal in the second vessel into the second solvent after the pouring of the second solvent and the closing of the second vessel. In this case, after the specimen liquid is distributed to the second vessel, various processes required for the specimen liquid in the second vessel can be carried out automatically.

The first and second transfer means may include first and second transfer paths for the first and the second vessels, respectively. In this case, the first and the second vessels are transferred in a state where a plurality of the first and the second vessels are held in a holder such as a tray and stand.

On the other hand, the first and second transfer means may include a transfer robot instead of the first and the second transfer paths. The transfer robot has an access range which covers each of the sections. In this case, the transfer robot transfers the holder together with the first or the second vessels.

The pretreatment system of the present invention can use a stoppered test tube as the first or the second vessel. The stoppered test tube includes a plug for closing the opening of the test tube, the plug having a neck and head.

When the stoppered test tube is used, the section which requires opening and closing the plug of the test tube includes a plug opener device having a wedge member. The wedge member wedges between the head of the plug and an opening edge of the test tube, and pushes out the plug from the opening of the test tube. With the plug opener device, even if the plug clings to the opening of the test tube, it is possible to reliably push out the plug from the opening of the test tube by the operation of the wedge member.

Further scope of applicability of the present invention will become apparent from the detailed description given hereinafter. However, it should be understood that the detailed description and specific example, while indicating preferred embodiment of the invention, are given by way of illustration only, since various changes and modifications within the sprit and scope of the invention will become apparent to those skilled in the art from this detailed description.

BRIEF DESCRIPTION OF THE DRAWINGS

The present invention will becomes more fully understood from the detailed description given hereinbelow and the accompany drawings which are given by way of illustration only, and thus, are not limitative of the present invention, and wherein:

FIG. 5 is a front view of a shaking apparatus for the system shown in FIG. 1;

FIGS. 7A, 7B and 7C are views showing procedural steps for shaking the distribution vial;

FIG. 23 is a schematic view showing an automatic pretreatment system according to a third embodiment.

DETAILED DESCRIPTION OF THE PREFERRED EMBODIMENTS

Automatic Pretreatment System According to First Embodiment

Figure 1:
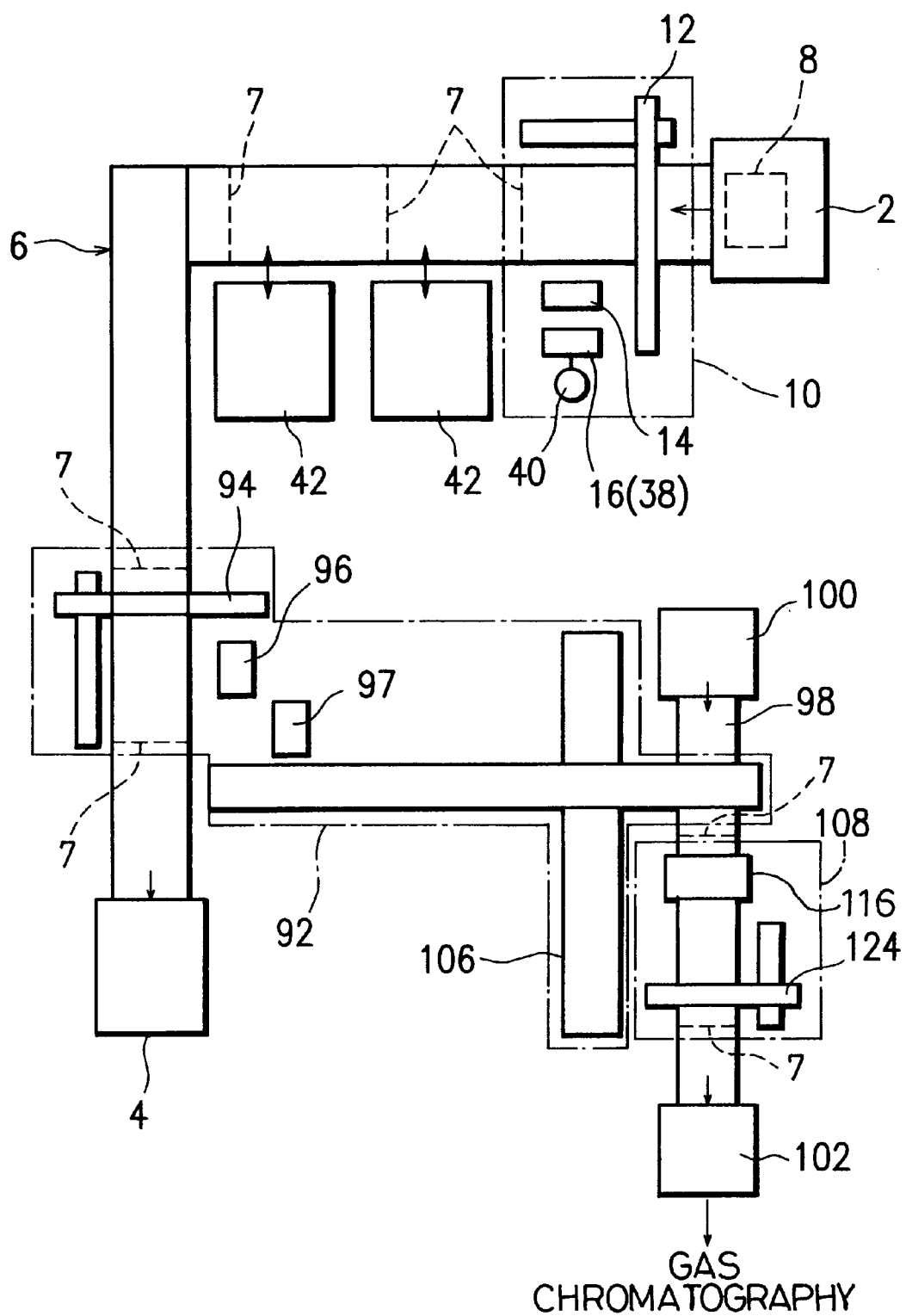
FIG. 1 is a schematic view showing an automatic pretreatment system according to a first embodiment.
Figure 2:
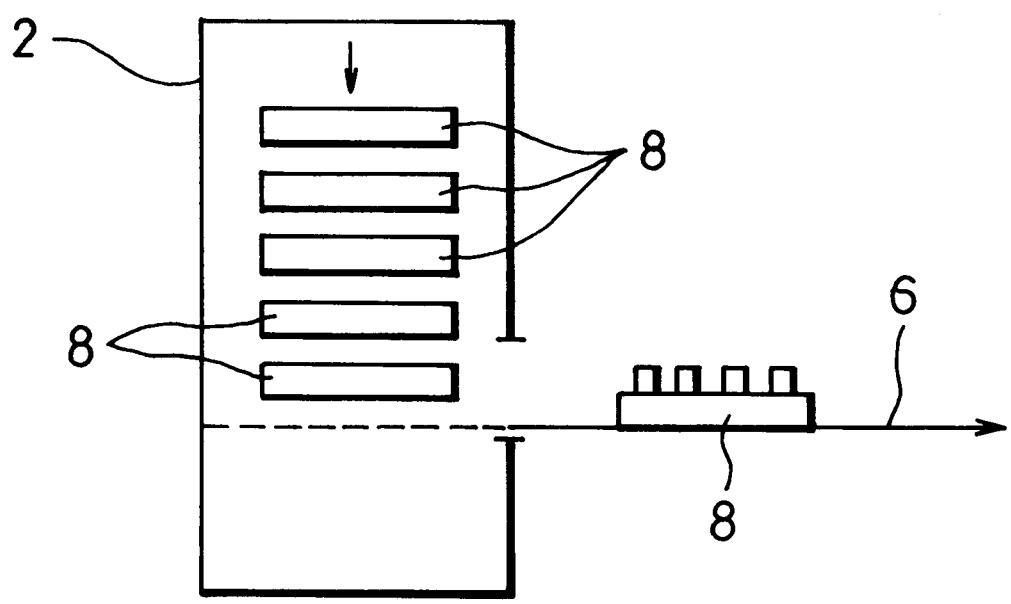
FIG. 2 is a schematic view showing a stocker storing trays for a distribution vial in the system shown in FIG. 1.

Referring to FIG. 1, an automatic pretreatment system for analyzing components of a specimen includes a sending stocker 2 and a receiving stocker 4. These stockers 2 and 4 are interconnected through a transfer path 6 which is a roller conveyer, for example. As shown in FIG. 2, many trays 8 are vertically accommodated in the sending stocker 2. The sending stocker 2 sends out the lowermost tray 8 onto the transfer path 6 and then, other trays 8 in the sending stocker 2 are lowered. Therefore, the trays 8 in the sending stocker 2 are sent out one by one, and the tray 8 sent out is transferred on the transfer path 6 toward the receiving stocker 4. The receiving stocker 4 receives the tray 8 from the transfer path 6 and the tray 8 is then accommodated vertically in the receiving stocker 4.

Each of the trays 8 is formed at its upper surface with many holes, and such holes are arranged in the form of a matrix, for example. A distribution vial is inserted in each of the holes, and is held uprightly. The distribution vial includes a screw cap mounted to an opening of the distribution vial. The distribution vials are previously held in all of the holes of each of the trays 8 in the sending stocker 2. Further, a specimen is previously accommodated in each of the distribution vials. For example, the specimen is a filter material of a filter-tipped cigarette smoked by an automatic smoking tester, and components of smoke of the cigarette are absorbed in the filter material.

The transfer path 6 is provided at a plurality of positions thereof with stoppers 7 which can temporarily stop the transfer of the tray 8 on the transfer path 6. In FIG. 1, the stoppers 7 are indicated with broken lines only.

Pouring Section of Solvent

The transfer path 6 is provided at its upstream position with a pouring section 10. The pouring section 10 includes a robot 12 disposed above the transfer path 6. The robot 12 has a hand which can be moved in three directions including a direction along the transfer path 6, a direction crossing the transfer path 6 and a vertical direction, i.e., X, Y and Z directions. The pouring section 10 further includes a stage 14 for attaching and detaching the screw cap, and a stage 16 for pouring a solvent. These stages 14 and 16 are disposed on the one side of the transfer path 6.

Figure 3:
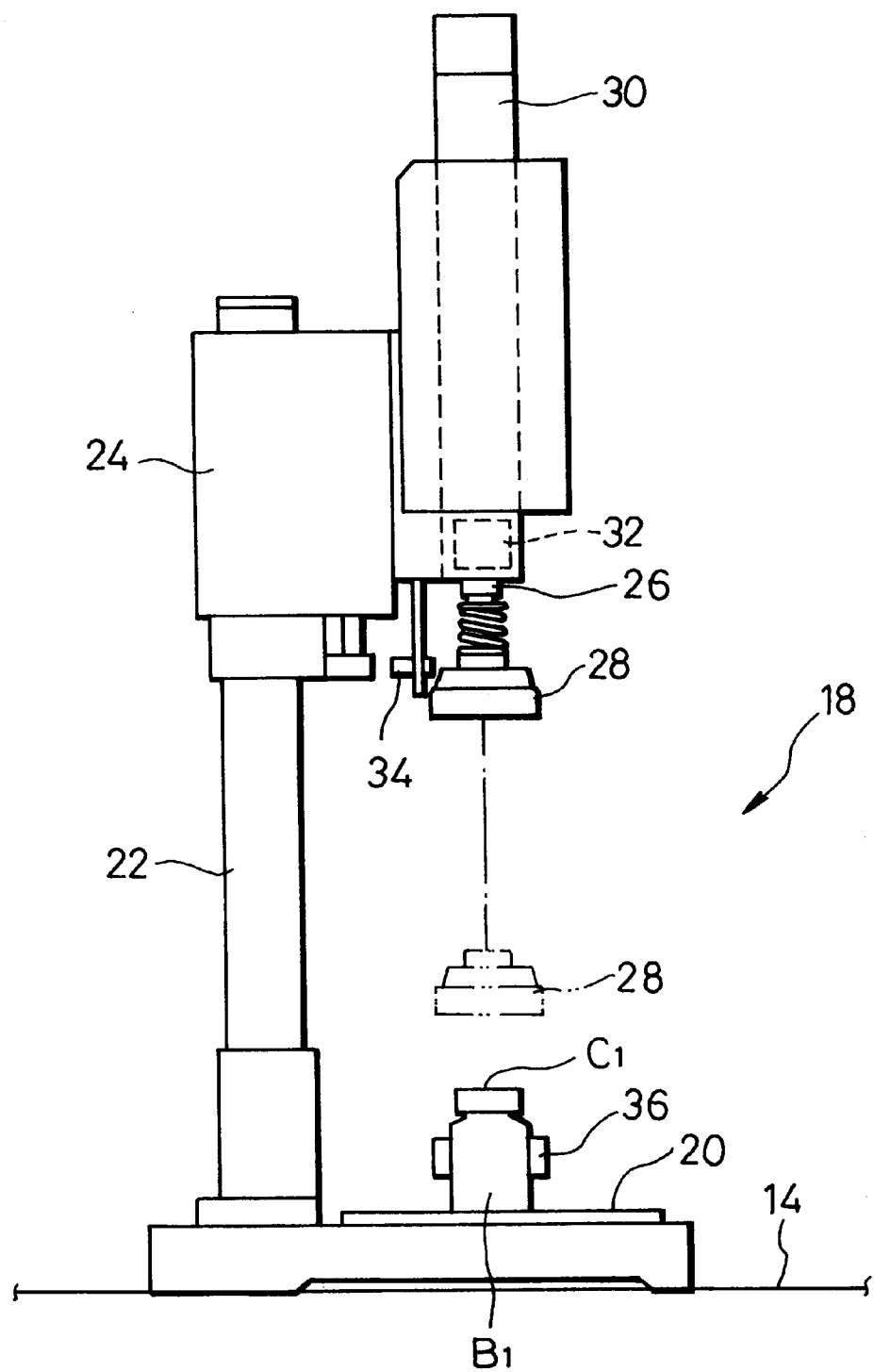
FIG. 3 is a side view of a capper for opening and closing a cap of the distribution vial.

As shown in FIG. 3, a capper 18 is disposed on the stage 14. The capper 18 includes a table 20, and a supporting post 22 extends upward from the table 20. The supporting post 22 is provided at its upper portion with a motor head 24 which includes a driving shaft 26. The driving shaft 26 extends in a vertical direction, and is supported by a casing of the motor head 24 for vertical movement and rotational movement. A chuck 28 is mounted to the lower end of the driving shaft 26 through a coil spring. The chuck 28 can be opened and closed. The motor head 24 further includes an air cylinder 30. A piston rod of the air cylinder 30 is connected to the driving shaft 26 such that the connection allows the driving shaft 26 to rotate. The motor head 24 is provided therein with an electric motor which can rotate both in forward and backward directions. A driving force of the electric motor is transmitted to the driving shaft 26 through a power transmission system (not shown) in the motor head 24, thereby the driving shaft 26 is rotated in forward and backward directions together with the chuck 28. The capper 18 further includes a torque sensor 32 and a proximity sensor 34. The torque sensor 32 detects a rotational torque of the driving shaft 26. The proximity sensor 34 detects the chuck 28 when the chuck 28 is at its upper position as shown in FIG. 3.

Figure 4A:
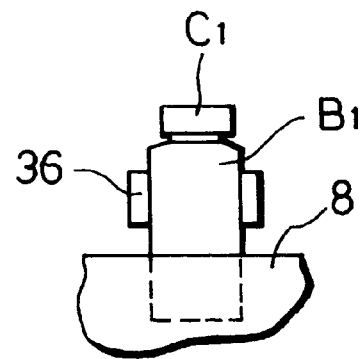
FIGS. 4A, 4B and 4C are views showing procedural steps for pouring a solvent into the distribution vial.

When one of the trays 8 on the transfer path 6 reaches the pouring section 10, the transfer of the tray 8 is stopped by the stopper 7. In a state where the tray 8 is stopped, the hand 36 of the robot 12 grasps selected one of the distribution vials $B_1$ on the tray 8 and takes the vials $B_1$ out from the tray 8 as shown in FIG. 4A. Then, the hand 36 places the distribution vial $B_1$ on the table 20 of the capper 18 as shown in FIG. 3. When the distribution vial $B_1$ is positioned at a predetermined position on the table 20 as grasped by the hand 36, the chuck 28 of the capper 18 is opened at its up position.

Figure 4B:
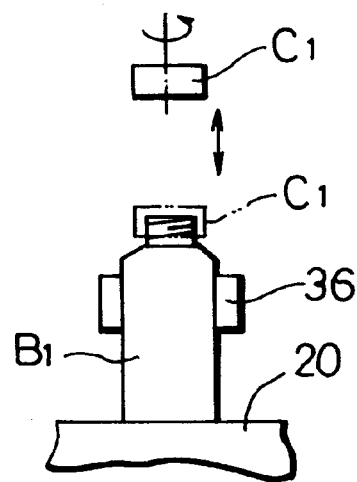

When the chuck 28 is lowered from the upper position, the chuck 28 surrounds the screw cap $C_1$ of the distribution vial $B_1$ and is closed simultaneously, thereby grasping the screw cap $C_1$. In this state, the chuck 28 rises while rotating together with the screw cap $C_1$, and the screw cap $C_1$ is removed from the opening of the distribution vial $B_1$ as shown in FIG. 4B. When the chuck 28 reaches the upper position together with the screw cap $C_1$, the proximity sensor 34 detects the chuck 28, and outputs a detection signal. Upon reception of this detection signal, the rising and rotation movements of the chuck 28 are stopped. The screw cap $C_1$ is on standby in a state where it is held by the chuck 28.

When the detection signal is output from the proximity sensor 34, the hand 36 of the robot 12 moves the distribution vial $B_1$ on the table 20 toward the pouring stage 16, and places the distribution vial $B_1$ on a predetermined position on the pouring stage 16.

Figure 4C:
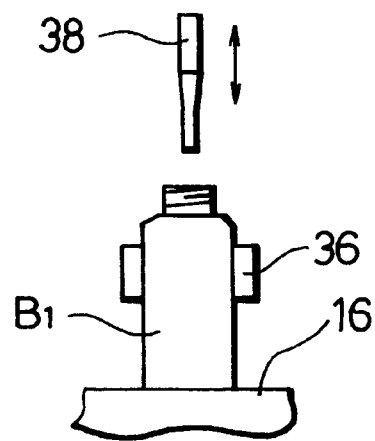

A solvent syringe 38 (see FIG. 1) and a solvent supply source 40 are arranged in the vicinity of the pouring stage 16, and the solvent supply source 40 supplies solvent to the syringe 38. The syringe 38 is held by a robot arm (not shown), and the robot arm can move the syringe 38 in vertical and horizontal directions above the pouring stage 16. As shown in FIG. 4C, the syringe 38 is positioned above the distribution vial $B_1$ on the pouring stage 16 from a standby position thereof and then, is lowered toward the opening of the distribution vial $B_1$. When the tip end of the syringe 38 enters into the distribution vial $B_1$, the syringe 38 pours the solvent into the distribution vial $B_1$ by a constant amount. Thereafter, the syringe 38 returns to the standby position.

When the pouring of the solvent is completed, the hand 36 of the robot 12 returns the distribution vial $B_1$ onto the table 20 of the capper 18. The chuck 28 of the capper 18 is lowered while rotating together with the screw cap $C_1$. At this time, the rotational direction of the chuck 28, i.e., of the screw cap $C_1$ is opposite from the rotating direction when the screw cap $C_1$ is removed as described above. Then, the screw cap $C_1$ is put on the opening of the distribution vial $B_1$ and mounted to the opening thereof. When an output from the above described torque sensor 32, i.e., a torque for fastening the screw cap $C_1$ reaches a predetermined value, the chuck 28 is opened to release the screw cap $C_1$. Thereafter, the rotation of the chuck 28 is stopped, the chuck 28 rises to the upper position for standby. On the other hand, the distribution vial $B_1$ supplied with the solvent is returned to the tray 8 on the transfer path 6 by the hand 36 of the robot 12.

The above described pouring process of solvent is repeatedly carried out with respect to all of the distribution vials $B_1$ on the tray 8. Thereafter, stopper 7 releases the tray 8 in the pouring section 10, and the tray 8 is again transferred on the transfer path 6. When the tray 8 is sent out from the pouring section 10, the next tray 8 is sent out onto the transfer path 6 from the sending stocker 2, and is supplied to the pouring section 10. Upon reception of the next tray 8, the pouring section 10 repeatedly carries out the pouring operation of solvent with respect to each of the distribution vials $B_1$ on the next tray 8.

Shaking Section

The shaking section is provided on a downstream side of the pouring section 10. The shaking section includes two shaking apparatuses 42 disposed along the transfer path 6. When a tray 8 on the transfer path 6 reaches one of the shaking apparatuses 42, the transfer of the tray 8 is stopped by the corresponding stopper 7.

Figure 6:
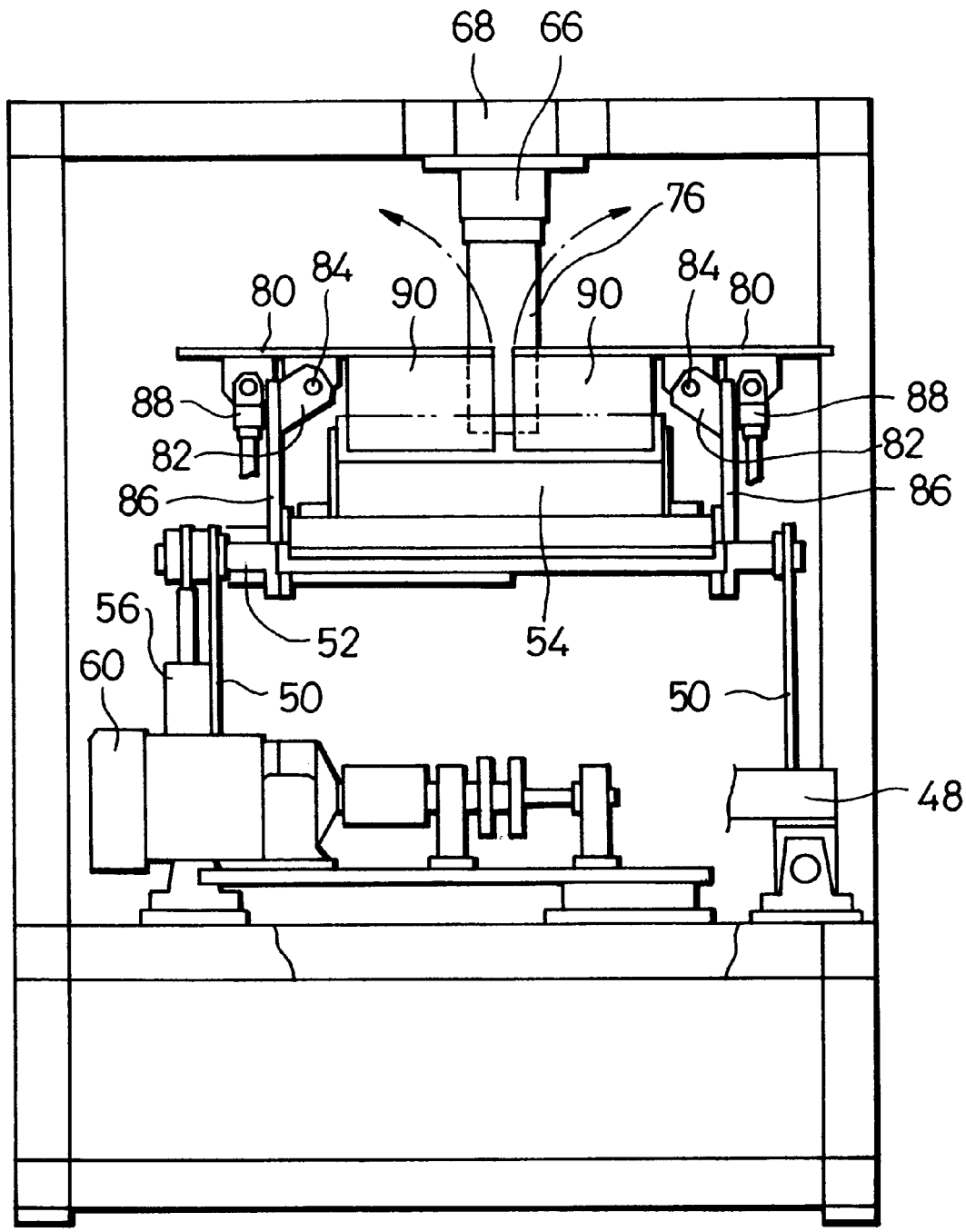
FIG. 6 is a side view of the shaking apparatus shown in FIG. 5.

Both the shaking apparatuses 42 have the same structures, and one of the shaking apparatuses is illustrated in detail in FIGS. 5 and 6. The shaking apparatuses 42 includes a base 44 disposed below the transfer path 6. A pair of guide rods 46 are horizontally disposed on the base 44, and extend perpendicular to the transfer path 6. Opposite ends of each of the guide rods 46 are supported on the base 44 through supporting legs 47. A carriage 48 is mounted to the guide rods 46, and the carriage 48 is capable of reciprocating along the guide rods 46. That is, the carriage 48 can move in both directions toward and away from the transfer path 6.

A pair of columns 50 extend upward from the carriage 48, and these columns 50 are separated away in a direction perpendicular to the moving direction of the carriage 48. The columns 50 are connected through a horizontal pivot shaft 52 whose opposite ends are rotatably supported at upper ends of the columns 50.

A tilt table 54 is mounted to the pivot shaft 52 and can rotate around the pivot shaft 52. The tilt table 54 and the carriage 48 are connected through an air cylinder, i.e., tilt cylinder 56 which supports the tilt table 54. When the tilt table 54 is in a state shown in FIG. 5, it is held in a horizontal position, and an upper surface of the tilt table 54 is positioned within a horizontal plane at the same height as the transfer plane of the transfer path 6.

The carriage 48 is connected to one end of a crank rod 58 which extends to the opposite direction from the transfer path 6. The other end of the crank rod 58 is connected to an outer peripheral portion of a crank disk 59 mounted to an output shaft of the electric motor 60. When the electric motor 60 rotates the crank disk 59 in one direction, the rotation of the crank disk 59 is converted into a reciprocating motion of the carriage 48 through the crank rod 58. A proximity sensor 62 is disposed on the base 44. When the carriage 48 reaches a reference position, the proximity sensor 62 detects the carriage 48 and outputs the detection signal.

As shown in FIG. 5, a roller conveyer 64 is disposed between the transfer path 6 and the shaking apparatus 42. When the tilt table 54 is in the horizontal position, the roller conveyer 64 provides a connection path between the transfer path 6 and the tilt table 54. In this state, the tray 8 stopped on the transfer path 6 in the shaking section can be transferred onto the tilt table 54 through the roller conveyer 64, and the tray 8 on the tilt table 54 can return onto the transfer path 6 through the roller conveyer 64.

A guide rail 66 is disposed above the transfer path 6 and the tilt table 54. The guide rail 66 horizontally extends in a direction perpendicular to the transfer path 6. The guide rail 66 is mounted to a beam member 68 supported on the base 44 through a column. A carrier 70 is mounted to the guide rail 66 and can reciprocate along the guide rail 66.

The carrier 70 includes a pusher 72 having pusher plates 74 and 76. The pusher plates 74 and 76 are opposed to each other at a distance in a direction perpendicular to the transfer path 6. The pusher plate 76 closer to the tilt table 54 is directly mounted to the carrier 70. The pusher plate 74 is mounted to the pusher plate 76 through an air cylinder 78. The air cylinder 78 is capable of adjusting a distance between the pusher plates 74 and 76.

When the pusher 72 is in a state shown in FIG. 5, pusher plates 74 and 76 thereof are positioned at opposite sides of the transfer path 6. The pusher 72 moves toward the tilt table 54 together with the carrier 70, and then the pusher plate 74 thereof abuts against a lateral side of the tray 8 along the transfer path 6 to push out the tray 8 together with the distribution vials $B_1$ from the transfer path 6 onto the tilt table 54 through the roller conveyer 64. When the tray 8 on the tilt table 54 abuts against a stopper (not shown), the pushing motion of the tray 8 by the pusher plate 74 is stopped. Thereafter, when a piston rod of the air cylinder 78 is extended, the pusher plate 74 is separated from the lateral side of the tray 8 as shown by two-dot lines in FIG. 5, and a predetermined distance is secured between the pusher plate 74 and the tray 8. When the tray 8 is transferred onto the tilt table 54, front and rear sides of the tray 8 are respectively guided by guide grooves (not shown) of the tilt table 54. These guide grooves restrain the movement of the tray 8 in a direction perpendicular to the guide grooves on the tilt table 54.

Then, on the tilt table 54, the distribution vials $B_1$ of the tray 8 are pressed from above by a pair of plate-like press pads 80. Therefore, the distribution vials $B_1$ are sandwiched between the press pads 80 and the tilt table 54 through the tray 8.

As is apparent from FIG. 6, each of the press pads 80 is mounted to a bracket 82 through a pin 84. These brackets 82 are disposed at opposite sides of the tilt table 54, and are mounted to support plates 86, respectively. These support plates 86 are mounted to sides of the tilt table 54 and extend upward from the tilt table 54. Each of the press pads 80 and the tilt table 54 are connected by means of air cylinders 88. Further each of the press pads 80 includes a stopper plate 90. The stopper plate 90 abuts against the lateral side of the tray 8 on the tilt table 54 to prevent the tray 8 from moving out from the tilt table 54.

When the tray 8 is transferred onto the tilt table 54, piston rods of the air cylinders 88 have been retracted, and the press pads 80 have been turned together with the stopper plates 90 upward around the pins 84. Turning motions of the stopper plates 90 open the moving path of the tray 8 between the transfer path 6 and the tilt table 54. Therefore, when the tray 8 on the transfer path 6 is transferred onto the tilt table 54, the tray 8 does not interfere with the stopper plates 90 as shown in FIG. 7A.

Thereafter, the piston rods of the air cylinders 88 are extended, and the press pads 80 are turned downward together with the stopper plates 90. Therefore, as shown in FIG. 7B, the press pads 80 press the distribution vials $B_1$ of the tray 8 on the tilt table 54, and the stopper plates 90 contact the lateral side of the tray 8.

When the above described air cylinder 56 is retracted, the tilt table 54 is rotated together with the tray 8 downward by 900 around the pivot shaft 52 to posture a vertical position as shown in FIG. 7C. At this time, the pressure plates 74 of the pusher 72 are sufficiently separated from the tray 8 and thus, the pressure plate 74 does not interfere with the press pads 80. When the tilt table 54 is in its vertical position, the lateral side of the tray 80 is supported by the stopper plates 90 and thus, the tray 8 should not drop from the tilt table 54.

When the electric motor 60 is driven, the carriage 48 reciprocates along the guide rods 46 as described above. The reciprocating motion of the carriage 48 shakes the distribution vials $B_1$ of the upright tray 8, which facilitate dissolution of the specimen components of the specimen into the solvent in the distribution vials $B_1$. Here, the shaking of the distribution vials $B_1$ is continuously carried out at predetermined frequency and amplitude for a predetermined time.

When the shaking process is completed, the rotational speed of the electric motor 60 is lowered, and the moving speed of the carriage 48 is limited to a predetermined speed or less. During the low speed mode, when the above described proximity sensor 62 outputs a detection signal of the carriage 48, the driving of the electric motor 60 is immediately stopped at the instant, and the carriage 48 returns to the reference position.

Next, the tilt table 54 returns to the horizontal position, and the press pads 80 release the pressing operation against the distribution vials $B_1$. In this state, the pusher 72 moves toward the transfer path 6, the pusher plate 76 abuts against the other lateral side of the tray 8 on the tilt table 54 to push the tray 8 with the distribution vials $B_1$ back onto the transfer path 6. The tray 8 on the transfer path 6 is released from the stopper 7 and is again transferred on the transfer path 6.

When one of the shaking apparatuses 42 is in use, the next tray 8 maybe transferred to the shaking section. In this case, the next tray 8 with the distribution vials $B_1$ is similarly loaded on the other shaking apparatus 42 in a similar manner, and the shaking processes for two trays are simultaneously carried out in the shaking section.

Distribution Section

As shown in FIG. 1, a distribution section 92 is provided on a side of the shaking section. The distribution section 92 has an operation area covering from the transfer path 6 to a transfer path 98.

The distribution section 92 includes a robot 94 provided above the transfer path 6, and a stage 96 disposed at the side of the transfer path 6. These robot 94 and the stage 96 are the same as the above described robot 12 and the stage 14 of the pouring section 10 and thus, descriptions thereof will be omitted. In the descriptions which will be made hereafter, any robot in any section also includes a hand which can move in X, Y and Z directions, unless it is described to the contrary.

When a tray 8 on the transfer path 6 reaches the distribution section 92, the transfer of the tray 8 is stopped by the stoppers 7. The hand of the robot 94 takes the distribution vial $B_1$ out from the tray 8 to supply the same to a capper (see FIG. 3) on the stage 96. The capper of the stage 96 takes the screw cap $C_1$ from the opening of the distribution vial $B_1$ and then, the hand of the robot 94 moves the distribution vial $B_1$ on the capper to the distributing stage 97. The distributing stage 97 is disposed in the vicinity of the stage 96.

The transfer path 98 connects a sending stocker 100 and a receiving stocker 102. These sending stocker 100 and the receiving stocker 102 are the same as the sending stocker 2 and the receiving stocker 4. Many trays are accommodated in the sending stocker 100, and a plurality of test vials are held in each of the trays. In this case, the test vial is an empty vial, and does not include a cap. The trays sent from the sending stocker 100 one by one are transferred on the transfer path 98 toward the receiving stocker 102.

The transfer path 98 is also provided at a plurality of positions thereof with stoppers 7 which are capable of temporarily stopping the transfer of the trays on the transfer path 98.

The distribution section 92 is provided with a robot 106. The robot 106 includes a distribution head 110 instead of a hand (see FIG. 8). The distribution head 110 can move in a region from the distributing state 97 to the transfer path 98. A syringe 112 is mounted to the distribution head 110, and has an exchangeable tip at its end.

Figure 8:
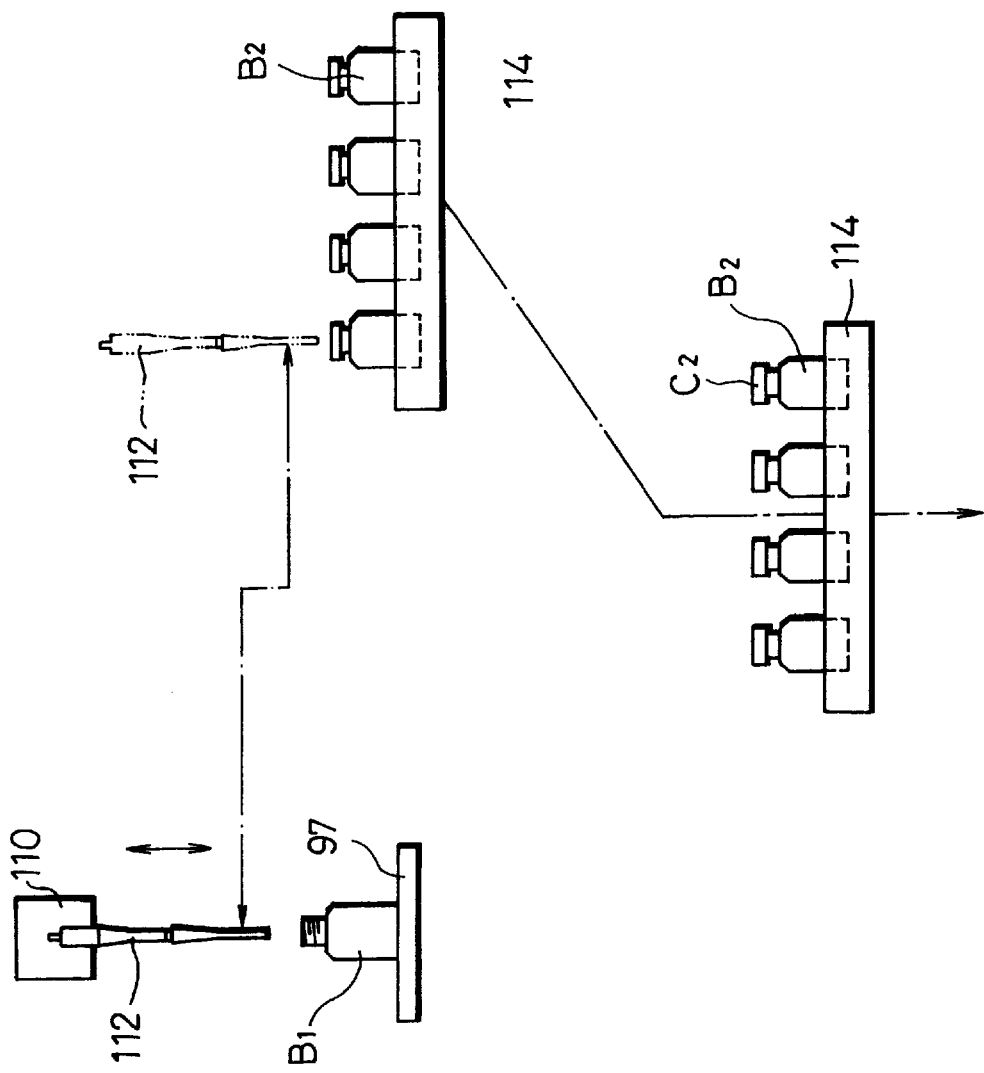
FIG. 8 is a view showing procedural steps for distributing a specimen liquid from the distribution vial to at least one test vial.

As shown in FIG. 8, the distribution head 110 moves the syringe 112 above the distribution stage 97. Next, the distribution head 110 is lowered by a predetermined distance, and the tip of the syringe 112 is immersed into the specimen liquid in the distribution vial $B_1$ on the stage 97. In this state, the distribution head 110 allows the syringe 112 to carry out a suction operation of the specimen liquid so that a predetermined amount of the specimen liquid is sucked into the tip of the syringe 112.

On the other hand, trays are sent out together with the test vials from the sending stocker 100, and the trays are transferred on the transfer path 98 toward the distribution section 92. When a tray reaches the distribution section 92, the transfer of the tray is temporarily stopped by the stoppers 7 of the transfer path 98. In FIG. 8, the trays on the transfer path 98 and the test vials are denoted by reference characters 114 and $B_2$, respectively.

The distribution head 110 is moved together with the syringe 112 above the tray 114 in the distribution section 92, and is lowered toward one of the test vials $B_2$ on the tray 114. When the tip of the syringe 112 enters into the test vial $B_2$, the lowering motion of the distribution head 110, i.e., of the syringe 112 is stopped. In this state, the distribution head 110 allows the syringe 112 to carry out the pouring operation of the specimen liquid, and a predetermined amount of the specimen liquid is poured into the test vial $B_2$. Thereafter, the distribution head 110 may also pour the specimen liquid into other test vials $B_2$ on the tray 114 in the similar manner if necessary.

During the pouring operation of the specimen liquid into the test vial $B_2$, the distribution vial $B_1$ on the distributing stage 97 is returned to the capper of the stage 96 by the hand of the robot 94, and the screw cap $C_1$ is again mounted to the opening of the distribution vial $B_1$ by this capper. Next, the distribution vial $B_1$ is returned to the tray 8 on the transfer path 6 by the hand of the robot 94.

The above described distributing process of the specimen liquid into one or a plurality of test vials $B_2$ from the distribution vial $B_1$ is repeatedly carried out with respect to all of the distribution vials $B_1$ on the tray 8. Whenever the distributing process is carried out, the tip of the syringe 112 of the distribution head 110 is replaced by a new one.

When the pouring process with respect to all of the distribution vials $B_1$ on the tray 8 is completed, the stopper 7 is release and then, the tray 8 is transferred on the transfer path 6 and then is accommodated in the receiving stocker 4.

Thereafter, when the next tray 8 reaches the distribution section 92, the distributing process is similarly repeated with respect to the distribution vials $B_1$ on the next tray 8.

Capping Section

On the other hand, when the specimen liquid is supplied into all of the test vials $B_2$ on the tray 114, the stopper 7 is released, and the tray 114 is transferred on the transfer path 98 toward the capping section 108. After the tray 114 passes through the capping section 108, a cap $C_2$ is mounted to the opening of each of the test vials $B_2$ on the tray 114 as shown in FIG. 8. Thereafter, the tray 114 is transferred together with the test vials $B_2$ on the transfer path 98, and is accommodated in the receiving stocker 102.

Figure 9:
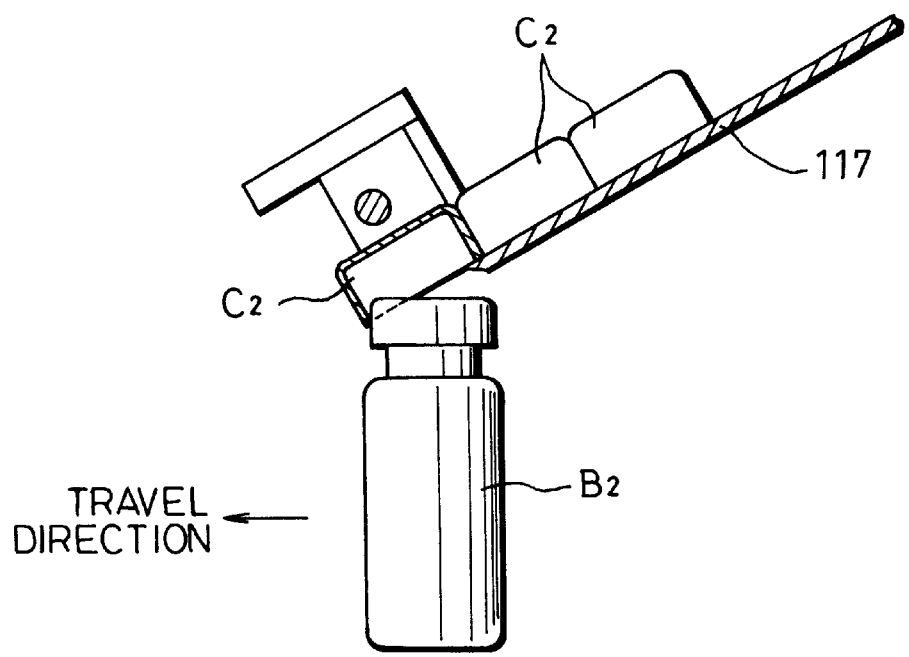
FIG. 9 is a view showing a portion of a supply section for supplying caps for the test vials.
Figure 10:
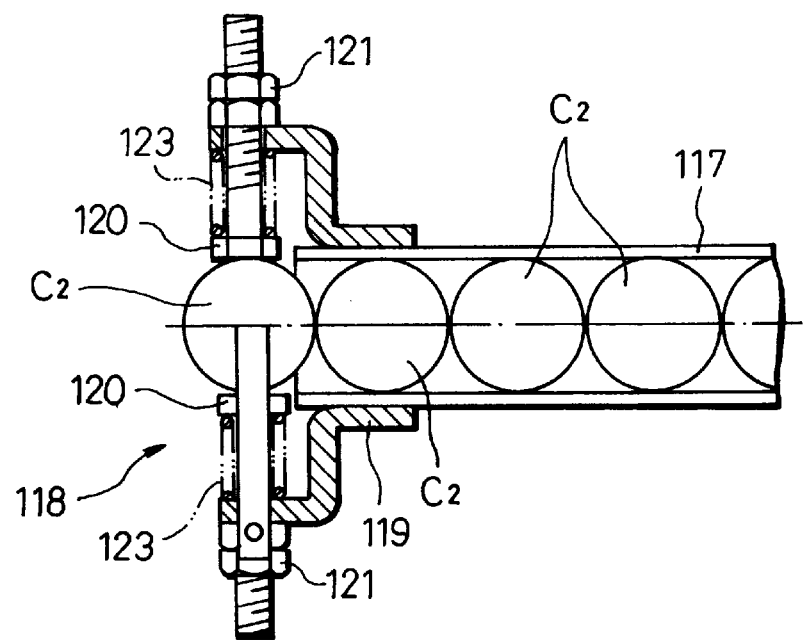
FIG. 10 is a plan view of the supply section which is partially sectioned.

The capping section 108 includes a supply chute array for the caps $C_2$, and the supply chute array extends along and above the transfer path 98. FIGS. 9 and 10 concretely show one supply chute 117 among the supply chute array. The supply chute 117 continuously supplies the caps $C_2$ toward the test vials $B_2$ arranged in one line along the transfer path 98 on the tray 114. The supply chute 117 is provided at its lower end portion with a clamp 118. The clamp 118 includes rod holders 119, and a pair of pinch rods 120 pass through the respective rod holders 119 and are mounted thereto. These pinch rods 120 are opposed with each other and an axis of the supply chute 117 is interposed between the pinch rods 120. A nut 121 is mounted to each of the pinch rods 120 for preventing the pinch rod 120 from loosening out from the rod holder 119. Further, a compression coil spring 123 is provided between the pinch rod 120 and the corresponding rod holder 119, respectively. The compression coil springs 123 bias the pair of pinch rods 120 in a direction approaching each other, thereby the nuts 121 of the pinch rods 120 are abutted against the rod holders 119, respectively.

The pair of pinch rods 120 sandwich the cap $C_2$ protruded from an exit of the supply chute 117, thereby preventing the cap $C_2$ from freely escaping from the supply chute 117. In this state, as shown in FIG. 9, when the test vial $B_2$ together with the tray 114 passes below the supply chute 117, the opening of the test vial $B_2$ catches the cap $C_2$ protruded from the exit of the supply chute 117, and takes this cap $C_2$ out from the clamp 118. Therefore, the cap $C_2$ is put on the opening of the test vial $B_2$ which has passed through the exit of the supply chute 117.

The capping section 108 is further provided at a downstream side of the supply chute array with a robot 124. A crimping tool is mounted to a hand of the robot 124. When the test vial $B_2$ which has received the cap $C_2$ is transferred to a position of the robot 124 with the tray 114, the transfer of the tray 114 is temporarily stopped. In this state, the crimping tool of the robot 124 crimps the caps $C_2$ to the test vials $B_2$ on the tray 114 in order, thereby completely mounting the caps $C_2$ to the test vials $B_2$.

After the caps $C_2$ are mounted to all of the test vials $B_2$ on the tray 114, the transfer of the tray 114 on the transfer path 98 is again started, and the tray 114 is accommodated in the receiving stocker 102 as described above.

The tray 114 in the receiving stocker 102 is taken out together with the test vials $B_2$, and the specimen liquid in the test vials $B_2$ is actually analyzed by gas chromatography.

In the above described automatic pretreatment system according to the first embodiment, it is possible to remove and mount the screw caps $C_1$ with respect to a plurality of distribution vials $B_1$, and pour the solvent simultaneously.

The automatic pretreatment system is used for distributing the specimen liquid including components of smoke of the cigarette. However, the automatic pretreatment system of the present invention can also be applied to pretreatment for analyzing various components in the medicinal or chemical field.

Automatic Pretreatment System According to Second Embodiment

Figure 11:
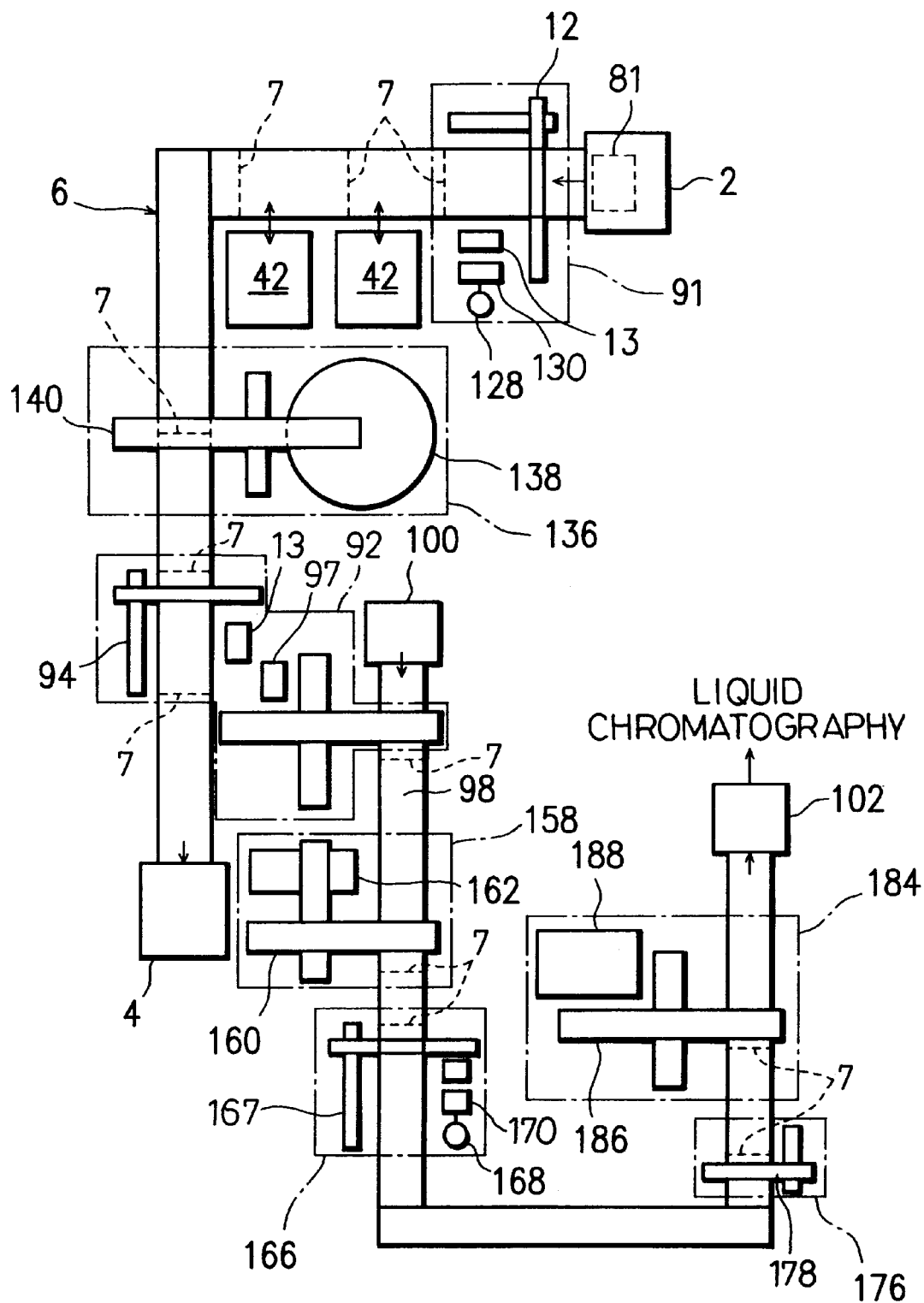
FIG. 11 is a schematic view showing an automatic pretreatment system according to a second embodiment.

FIG. 11 shows an automatic pretreatment system according to a second embodiment. This automatic pretreatment is used, for example, for distributing specimen liquid such as blood plasma samples. In the following description of the automatic pretreatment system of the second embodiment, like reference characters denote like parts having the same functions as those in the system of the above described first embodiment, and descriptions thereof will be omitted.

Figure 12:
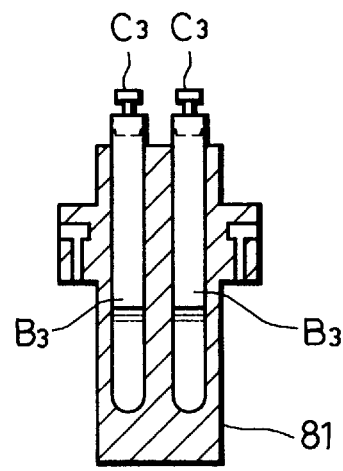
FIG. 12 is a view showing a tray and a distribution vial used in the system shown in FIG. 11.

In the case of the second embodiment, vial stands 81 instead of the trays 8 are sent out from the sending stocker 2 one by one. The vial stands 81 and the distribution vials $B_3$ are shown in FIG. 12. The vial stand 81 holds the distribution vials $B_3$ in two rows. The distribution vial $B_3$ is formed into a tube-shape made of transparent glass. The distribution vial $B_3$ includes a plug $C_3$ instead of the cap, and the plug $C_3$ is made of glass and is inserted into an opening of the distribution vial $B_3$. A predetermined amount of specimen is previously contained in each of the distribution vials $B_3$ in the vial stand 81.

First Pouring Section

Figure 13:
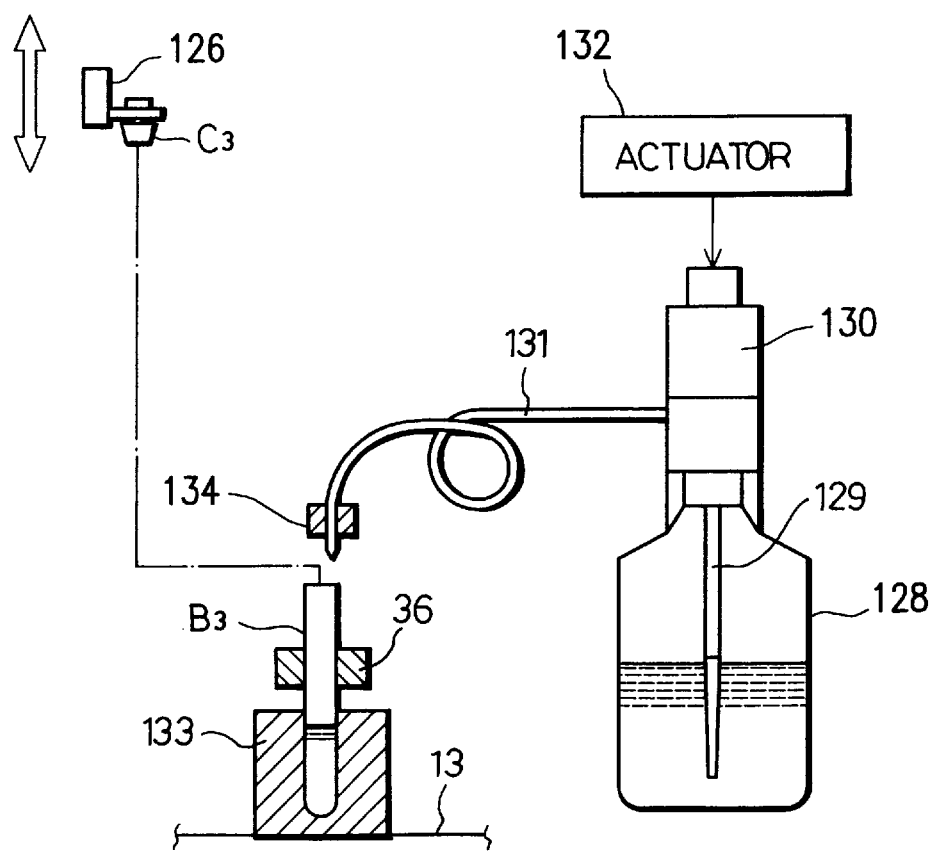
FIG. 13 is a view concretely showing a pouring section for a first solvent shown in FIG. 11.

The vial stand 81 is sent out onto the transfer path 6 from the sending stocker 2. The vial stand 81 on the transfer path 6 is transferred toward a first pouring section 91 where the transfer of the vial stand 81 is temporarily stopped. In the first pouring section 91, the hand 36 of the robot 12 takes the distribution vial $B_3$ out from the vial stand 81. As shown in FIG. 13, the taken out distribution vial $B_3$ is inserted into a holder 133 on a stage 13.

A chuck 126 is disposed above the stage 13, and can move up and down. The chuck 126 is lowered to grasp the plug $C_3$ of the distribution vial $B_3$ on the holder 133. Next, the chuck 126 rises to pull out the plug $C_3$ from the opening of the distribution vial $B_3$. If a clamp for clamping the distribution vial $B_3$ is built in the holder 133, the hand 36 of the robot 12 can be used instead of the chuck 126.

A solvent tank 128 is disposed in the vicinity of the stage 13, and first solvent is stored in the solvent tank 128. A syringe 130 is connected to the solvent tank 128. The syringe 130 includes a suction tube 129 and a pouring tube 131. The suction tube 129 extends into the solvent tank 128, and its suction opening is immersed into the first solvent. The pouring tube 131 extends outside the syringe 130, and a tip end, i.e., a nozzle of the pouring tube 131 is grasped by a hand 134 of a robot (not shown). The hand 134 of the robot permits the nozzle of the pouring tube 131 to enter into the distribution vial $B_3$ on the holder 133.

The syringe 130 further includes an actuator 132. The actuator 132 can permit the syringe 130 to independently carry out a suction operation and a pouring operation of the first solvent. Therefore, the syringe 130 is operated by the actuator 132 so that the syringe 130 sucks the first solvent through the suction tube 129, and pours a predetermined amount of the sucked first solvent into the distribution vial $B_3$ through the pouring tube 131.

The nozzle of the pouring tube 131 comes out from the distribution vial $B_3$, and the plug $C_3$ is again inserted into the opening of the distribution vial $B_3$. Next, the distribution vial $B_3$ is returned to the vial stand 81 on the transfer path 6.

Here, acid solvent or organic solvent is selected as the first solvent depending on a kind of the specimen. For example, the first solvent is hydrochloric acid (HCL), water ($H_2O$), ether or the like, or a mixed liquid thereof.

If a plurality of the distribution vials $B_3$ are arranged on the stage 13 through the holder 133, the pouring process of the first solvent can simultaneously be carried out with respect to these distribution vials $B_3$.

Further, the pouring process of the first solvent can also be carried out without taking out the distribution vials $B_3$ from the vial stand 81 on the transfer path 6.

After the pouring processes have been conducted for all of the distribution vials $B_3$ in the vial stand 81, the vial stand 81 is transferred on the transfer path 6 toward a shaking section.

Shaking Section

When the vial stand 81 on the transfer path 6 reaches the shaking section, the vial stand 81 are loaded on the shaking apparatus 42 from the transfer path 6, and the distribution vials $B_3$ of the vial stand 81 is subjected to a shaking treatment for a predetermined time in the shaking apparatus 42.

After the shaking treatments have been completed, the vial stand 81 is returned from the shaking apparatus 42 to the transfer path 6, and is transferred to a next section, i.e., a centrifuging section.

Since the vial stand 81 is loaded on the shaking apparatus 42 together with the distribution vials $B_3$, the tilt table 54, the press pad 80 and the like of the shaking apparatus 42 are changed into shapes suitable for the vial stand 81. In this case, one press pad 80 suffices.

Centrifuging Section

A centrifuging section 136 is disposed on a downstream side of the shaking section. When the vial stand 81 on the transfer path 6 reaches the centrifuging section 136, the transfer of the vial stand 81 is temporarily stopped. The section 136 includes a centrifugal separator 138 disposed at the side of the transfer path 6. The section 136 further includes a robot 140, and a hand of the robot 140 can move from the transfer path 6 to the centrifugal separator 138. The hand of the robot 140 grasps the vial stand 81 on the transfer path 6 and moves the stand 81 to the centrifugal separator 138 and then, loads the vial stands 81 into the centrifugal separator 138. In the centrifugal separator 138, specimen liquid in the distribution vials $B_3$ of the vial stands 81 is subjected to a centrifuging treatment. After that, the hand of the robot 140 takes the vial stands 81 out from the centrifugal separator 138, and returns the stands 81 on the transfer path 6.

Figure 14:
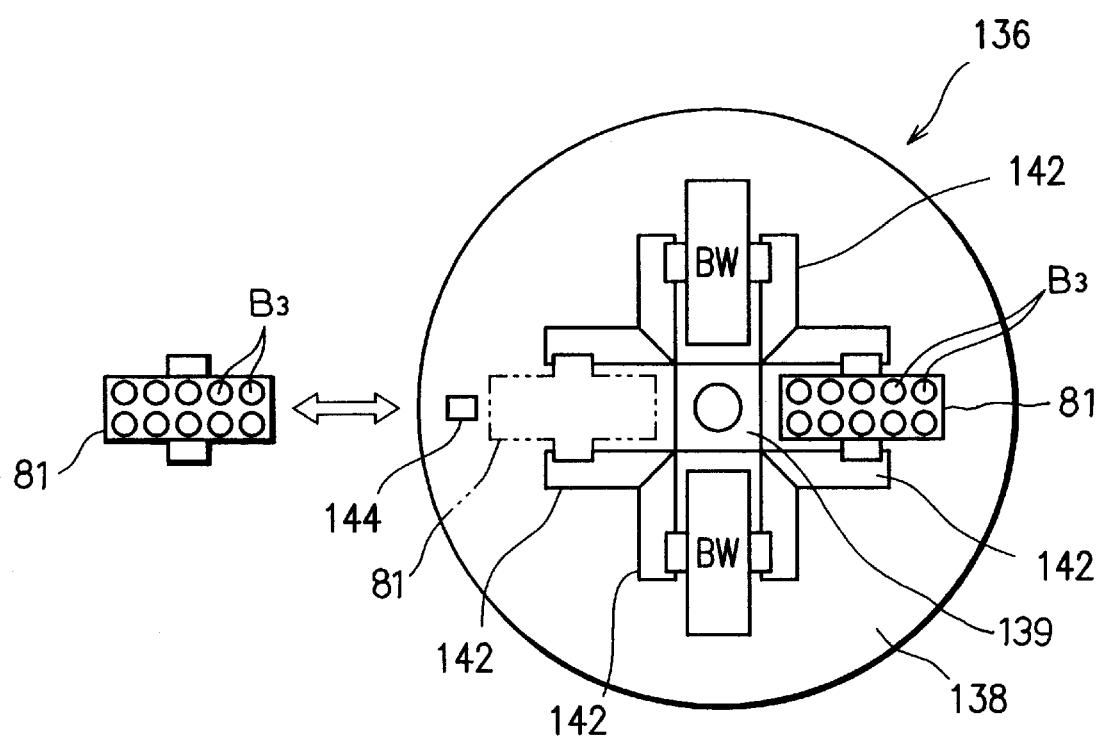
FIG. 14 is a view concretely showing a centrifugal separator shown in FIG. 11.

As shown in FIG. 14, the centrifugal separator 138 includes a rotor 139 which has, e.g., four stand holders 142. The stand holders 142 are arranged in the rotational direction of the rotor 139 at equal intervals. When an empty stand holder 142 comes to a predetermined angular position, loading or unloading of the vial stand 81 to that stand holder 142 is conducted. A detector 144 is provided in the centrifugal separator 138 for detecting the rotational angular position of the stand holders 142.

The rotor 139 of the centrifugal separator 138 is rotated in a state where two or all of the stand holder 142 receive the vial stands 81. When two stand holders 142 are used, the other two stand holders 142 each receive a balanced weight BW as shown in FIG. 14.

For loading and unloading of the vial stand 81 with respect to the centrifugal separator 138, the same mechanism as that for loading and unloading the vial stand 81 with respect to the shaking apparatus 42 can also be employed instead of the robot 140.

The vial stand 81 which has been subjected to the centrifuging process and returned onto the transfer path 6 is transferred toward the distribution section 92.

Distribution Section

When the vial stand 81 on the transfer path 6 reaches the distribution section 92, the transfer of the vial stand 81 is temporarily stopped. In the distribution section 92, the hand of the robot 94 takes out the distribution vial $B_3$ of the vial stand 81, and moves it onto the stage 13. Similarly to the case of the first charging section 91, the plug $C_3$ of the distribution vial $B_3$ on the stage 13 is taken out. Next, the hand of the robot 94 moves the distribution vial $B_3$ from the stage 13 to the stage 97.

Figure 15:
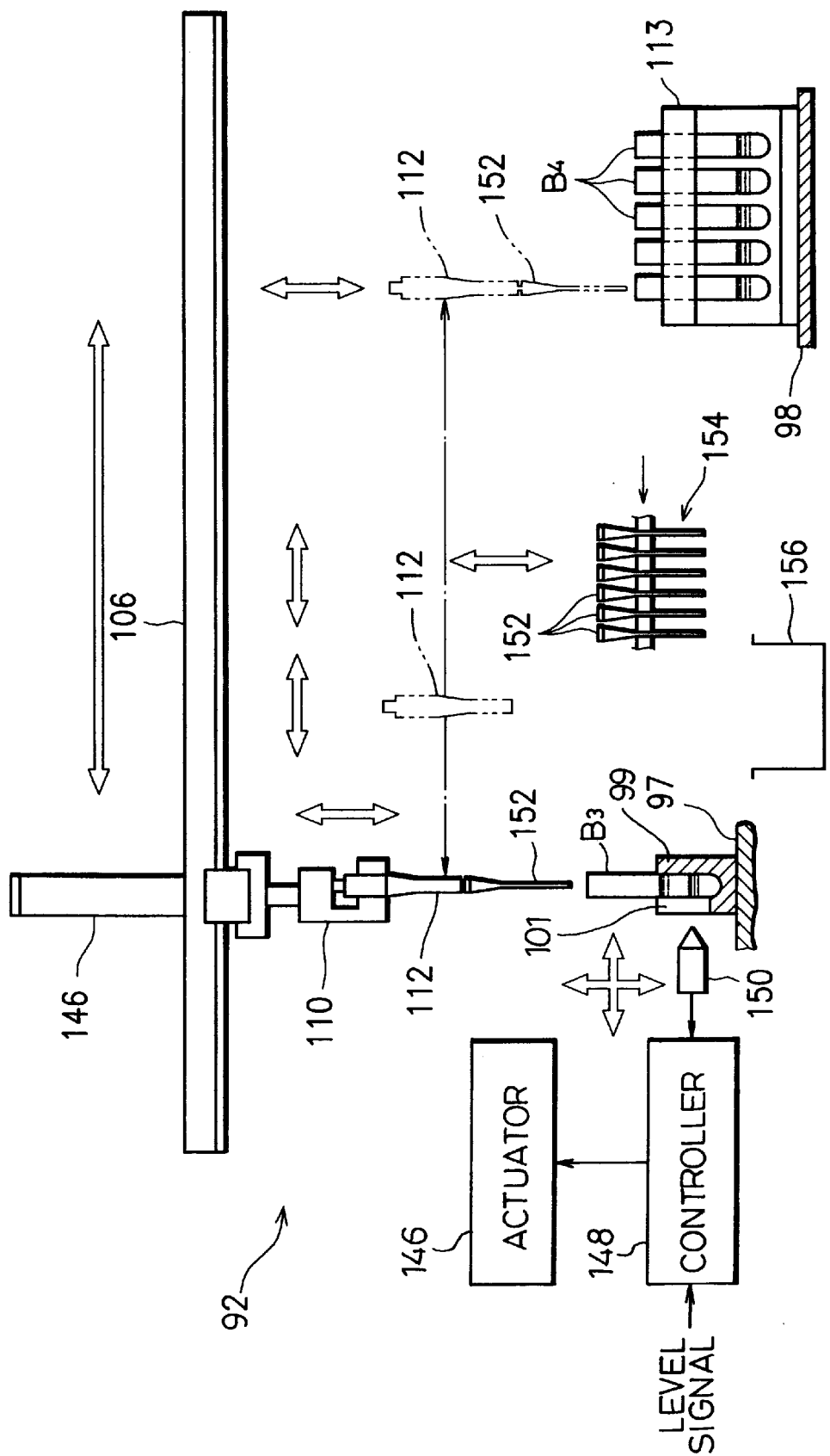
FIG. 15 is a view for explaining a distribution section shown in FIG. 11.

As shown in FIG. 15, a holder 99 is disposed on the stage 97, and the distribution vial $B_3$ is inserted into the holder 99. The holder 99 is formed with an aperture 101 which exposes a portion of the distribution vial $B_3$ outside the holder 99. An optical detector 150 is disposed in the vicinity of the holder 99 such as to oppose the aperture 101. The optical detector 150 detects a boundary or an interface between liquid layers of the specimen liquid in the distribution vial $B_3$. More since the specimen liquid in the distribution vial $B_3$ was subjected to the centrifugal process, the specimen liquid is separated into two liquid layers. The optical detector 150 detects the interface between the liquid layers in the distribution vial $B_3$, and supplies the detection signal to a controller 148.

Based on the detection signal from the optical detector 150, the controller 148 controls the operation of the actuator 146 for moving up and down the distribution head 110 of the robot 106, i.e., the syringe 112. Therefore, the insertion length of the syringe 112 into the distribution vial $B_3$ is controlled, and the tip end of the syringe 112 is positioned in one of the liquid layers in the distribution vial $B_3$. As a result, the syringe 112 can suck the specimen liquid from one of the liquid layers by a predetermined amount.

If the interface level between the liquid layers in the distribution vial $B_3$ is already known based on an amount of the specimen and an amount of the first solvent poured, the optical detector 150 can be omitted. In this case, a level signal indicative of the interface level in the distribution vial $B_3$ is supplied to the controller 148 from, e.g., an adjusting knob (not shown).

Thereafter, the syringe 112 is moved to a vial stand 113 on the transfer path 98, and pours the sucked specimen liquid into one or a plurality of test vials $B_4$ held by the vial stand 113. The test vial $B_4$ is made of glass into a tube-like shape as the distribution vial $B_3$. The vial stands 113 are sequentially sent out from the sending stocker 102 onto the transfer path 98.

FIG. 15 shows a supply path 154 of tips 152 which is not shown in FIG. 11. Prior to a sucking operation of the specimen liquid in the distribution vial $B_3$, the syringe 112 releases the tip 152 used and then takes out a new tip 152 from the supply path 154. The spent tip 152 is thrown out into a dumping box 156. Outline arrows in FIG. 15 indicate movements of the syringe 112 and the distribution vials $B_3$.

It is possible to fix the syringe 112 at a predetermined position, instead of mounting the syringe 112 to the distribution head 110. In this case, the robot 106 includes a hand instead of the distribution head 110, and the hand grasps the nozzle of the suction/pouring tube extending from the syringe 112.

When the distribution process has been completed, the distribution vial $B_3$ is returned from the stage 97 to the stage 13, and the plug $C_3$ is again inserted into the opening of the distribution vial $B_3$ on the stage 13. Next, the distribution vial $B_3$ is returned to the vial stand 81 on the transfer path 6. When the distribution processes have been carried out for all of the distribution vials $B_3$ of the vial stand 81, the vial stand 81 is transferred on the transfer path 6, and then is accommodated in the receiving stocker 4.

On the other hand, when the specimen liquid has been poured into all of the test vials $B_4$ of the vial stand 113, the vial stand 113 is transferred on the transfer path 98 toward a crystallizing section.

Crystallizing Section

When the vial stand 113 reaches the crystallizing section 158, the transfer of the vial stand 113 on the transfer path 98 is temporarily stopped. The crystallizing section 158 includes a robot 160 disposed above the transfer path 98, and a water bath 162 disposed at a side of the transfer path 98.

Figure 16:
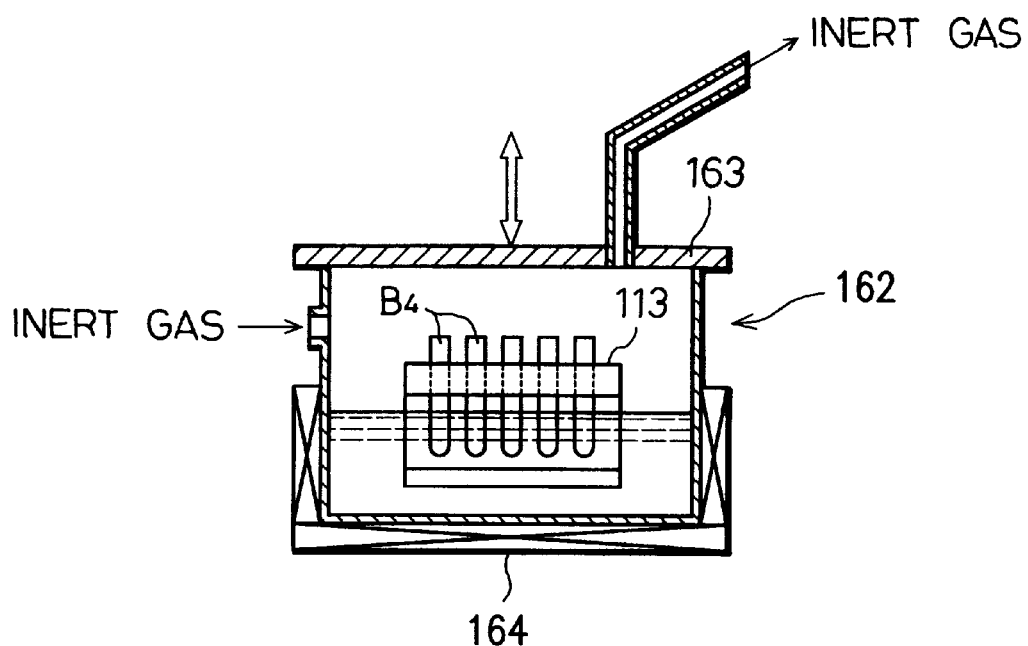
FIG. 16 is a view concretely showing a crystallizing section shown in FIG. 11.

As shown in FIG. 16, the water bath 162 includes a lid 163 which can open and close the water bath 162. The water bath 162 further includes a heater 164 heating water in the water bath 162 to a predetermined temperature.

In a state where the lid 163 of the water bath 162 is opened, the hand of the robot 160 grasps the vial stand 113 on the transfer path 98, and moves the vial stand 113 into the water bath 162. Next, the hand of the robot 160 is retracted from the water bath 162, the lid 163 of the water bath 162 is closed. The specimen liquid in the test vials $B_4$ of the vial stand 113 is heated in the water bath 162, such heating concentrates the specimen liquid in the test vials $B_4$, and the specimen liquid is dried and brought into a solid state. That is, the specimen liquid is crystallized. During the crystallizing process, air in the water bath 162 is substituted by inert gas such as nitrogen gas, and the specimen liquid is not oxidized.

When the crystallizing process has been completed, the vial stand 113 is returned onto the transfer path 98 together with the test vials $B_4$, and is transferred toward a second pouring section 166.

Second Pouring Section

Figure 17:
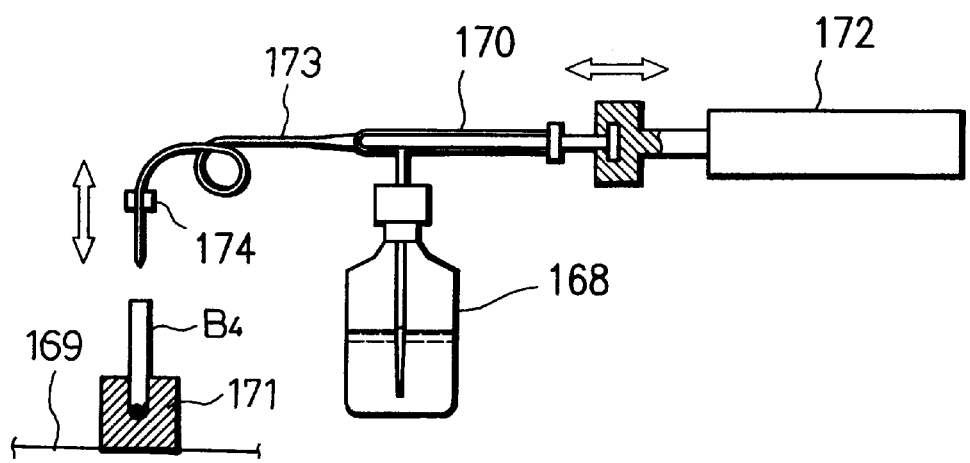
FIG. 17 is a view concretely showing a pouring section for a second solvent shown in FIG. 11.

When the vial stand 113 on the transfer path 98 reaches the second pouring section 166, the transfer of the vial stand 113 is temporarily stopped. The second pouring section 166 includes a robot 167, and a stage 169 disposed at a side of the transfer path 98. A hand of the robot 167 takes the test vial $B_4$ out from the vial stand 113, and inserts the test vial $B_4$ into a holder 171 of the stage 169 as shown in FIG. 17.

A solvent tank 168 is disposed in the vicinity of the stage 169, and a second solvent is stored in the solvent tank 168. Selected as the second solvent is a solvent which becomes a mobile phase at the time of analysis by liquid chromatography. A micro syringe 170 is connected to the solvent tank 168, and a suction operation and a pouring operation of the micro syringe 170 is conducted by an air cylinder 172. A pouring tube 173 extends from the micro syringe 170, and a tip end, i.e., a nozzle of the pouring tube 173 is grasped by the hand of the robot 174. The micro syringe 170 sucks the second solvent in the solvent tank 168, and pours the sucked second solvent into the test vial $B_4$ from the nozzle of the pouring tube 173 by a predetermined amount. Thereafter, the test vial $B_4$ is returned to the vial stand 113 by the hand of the robot 167.

When the second solvent has been charged into all of the test vials $B_4$ of the vial stand 113, the vial stand 113 is transferred on the transfer path 98 toward a plugging section 176 together with the test vials $B_4$.

Plugging Section

Figure 18:
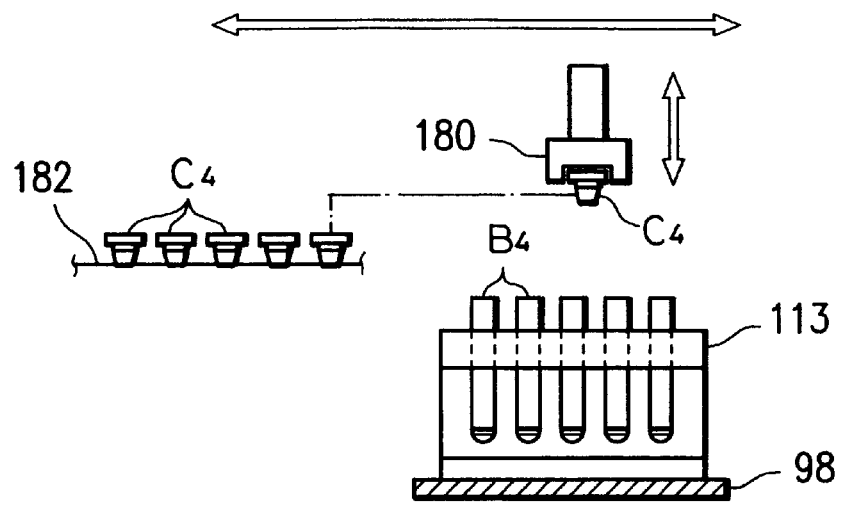
FIG. 18 is a view concretely showing a capping section shown in FIG. 11.

When the vial stand 113 on the transfer path 98 reaches the plugging section 176, the transfer of the vial stand 113 is temporarily stopped. The plugging section 176 includes a robot 178 disposed above the transfer path 98. As shown in FIG. 18, a hand 180 of the robot 178 grasps one of the plugs $C_4$ on a supply path 182, and inserts the plug $C_4$ into the opening of the test vial $B_4$ of the vial stand 113. The plug $C_4$ is made of glass. The supply path 182 sequentially supplies the plugs $C_4$ in one row.

When the plugs $C_4$ have been mounted to all of the test vials $B_4$ of the vial stand 113, the vial stand 113 is transferred on the transfer path 98 toward a dissolving section 184.

Dissolving Section

Figure 19:
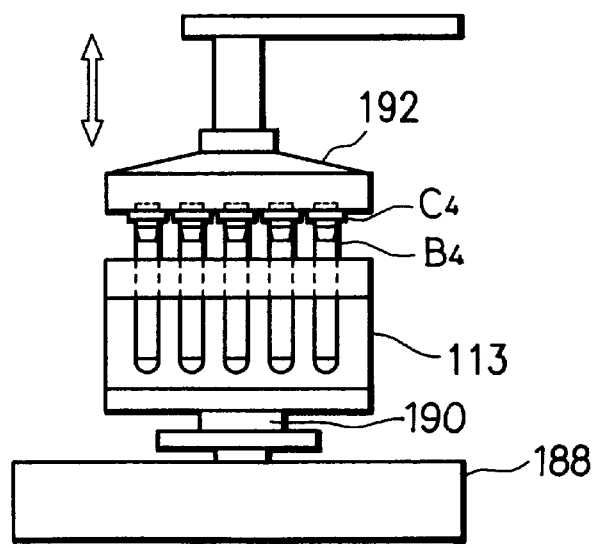
FIG. 19 is a view concretely showing a dissolving section of shown in FIG. 11.

When the vial stand 113 on the transfer path 98 reaches the dissolving section 184, the transfer of the vial stand 113 is temporarily stopped. The dissolving section 184 includes a robot 186 disposed above the transfer path 98, and a shaking apparatus 188 disposed at a side of the transfer path 98. As shown in FIG. 19, the shaking apparatus 188 includes a vertically shaking table 190, and a press lid 192 disposed above the table 190 for vertical movements.

A hand of the robot 186 grasps the vial stand 113 on the transfer path 98, and puts the vial stand 113 on the shaking table 190. Next, the press lid 192 is lowered to press the test vials $B_4$ of the vial stand 113. In this state, the shaking table 190 is vertically shaken together with the vial stand 113 for a predetermined time period. This shaking operation stirs the second solvent in the test vials $B_4$ and as a result, the crystal of the specimen liquid is dissolved into the second solvent. The press lid 192 is supported by the shaking table 190 so that the press lid 192 is shaken together with the shaking table 190.

When the dissolving process has been completed, the hand of the robot 186 returns the vial stand 113 from the shaking table 190 onto the transfer path 98. The vial stand 113 is transferred on the transfer path 98, and then is accommodated in the receiving stocker 102.

Next, the vial stand 113 is taken out from the receiving stocker 102 together with the test vials $B_4$, and the test vials $B_4$ of the vial stand 113 are supplied to the liquid chromatography.

According to the above described automatic pretreatment system of the second embodiment, each of the processes from the first pouring process to the dissolving process is automatically carried out.

In the case of the automatic pretreatment system of the second embodiment, processes after the centrifuging process are not necessarily required. If such processes are omitted, the vial stand on the transfer path simply skips over the sections of the omitted processes.

Plug Opener Device

Figure 20:
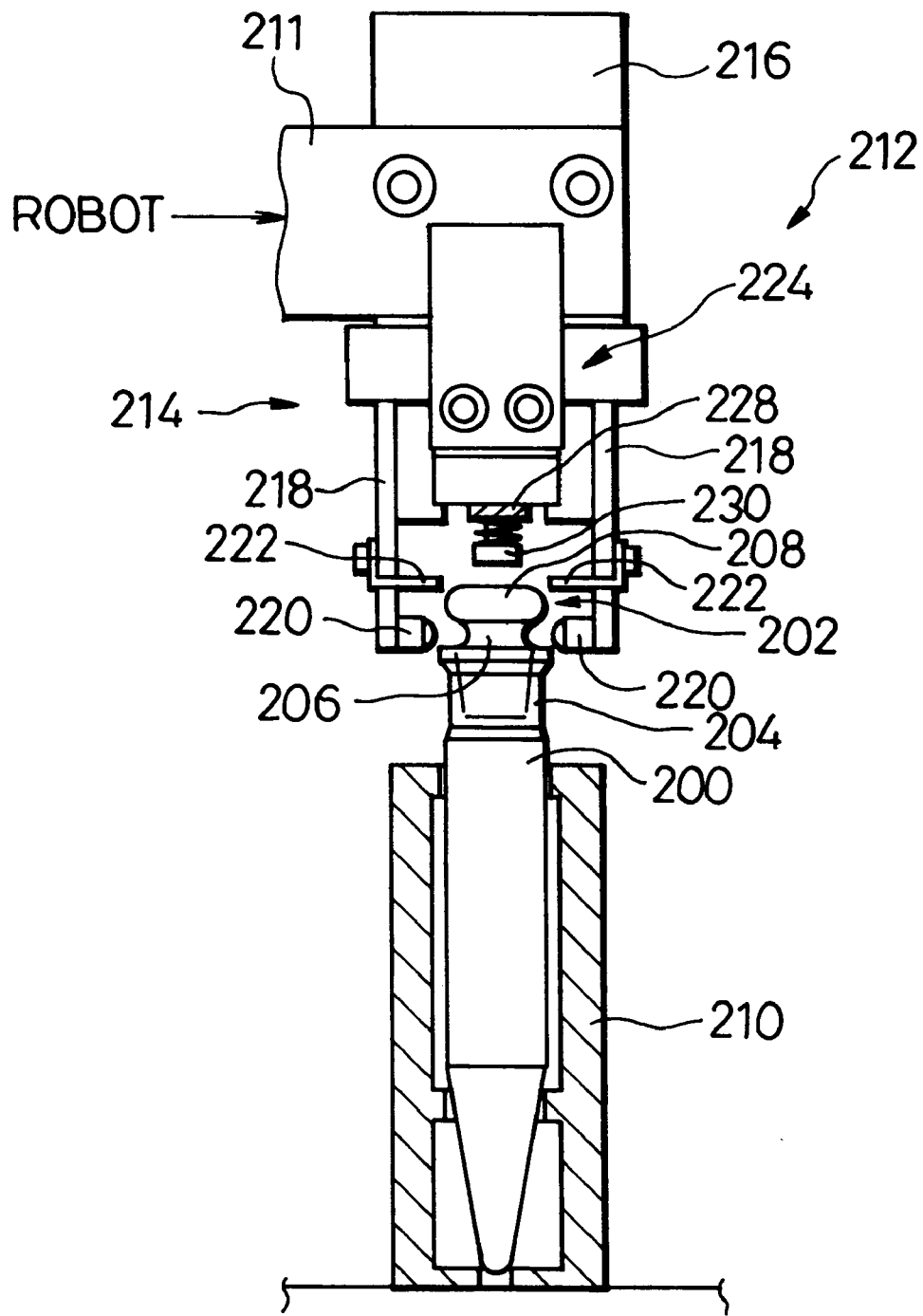
FIG. 20 is a front view of a plug opener device for opening and closing the plug of a stoppered test tube.

Next, referring to FIG. 20, there is shown a stoppered test tube 200 which is used instead of the distribution vial and the test vial. An opening of the stoppered test tube 200 is closed by a plug 202. More specifically, the plug 202 includes a plug body 204 to be inserted into the opening of the stoppered test tube 200, and a head 208 connected to the plug body 204 through a neck 206. In the case of such a stoppered test tube 200, the plug 202 is inserted into the opening of the tube 200 such that the plug 202 clings to the opening of the stoppered test tube 200. Therefore, even if the hand of the robot rises in a state where the hand grasps the head 208 of the plug 202, the stoppered test tube 200 may be brought up from the holder 210 together with the plug 202. In such a case, the opening of the stoppered test tube 200 can not be opened, and the pouring process or distribution process of solvent against the stoppered test tube 200 can not be conducted.

Figure 21:
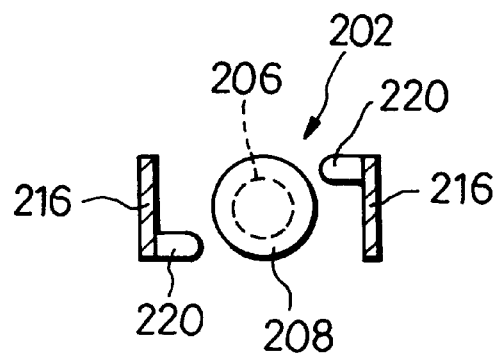
FIG. 21 is a view showing the arrangement of wedge pins provided for the plug opener device shown in FIG. 20.

In order to avoid such an inconvenience, a plug opener device 212 for the stoppered test tube 200 can be mounted to the hand of the robot or a robot arm 211. The plug opener device 212 includes a chuck 214 provided with a vertically disposed air cylinder 216, and a pair of chuck fingers 218 opened and closed by the operation of the air cylinder 216. More specifically, the chuck fingers 218 are opposed to each other, and extend from the air cylinder 216 downward. When the air cylinder 216 is operated, the pair of chuck fingers 218 move toward each other. A wedge pin 220 is mounted to the lower end of each of the chuck fingers 218. As shown in FIG. 21, the wedge pin 220 of one of the chuck fingers 218 projects toward the other chuck finger 218, and a distance corresponding to a diameter of the neck 206 of the plug 202 is secured between the axes of the wedge pins 220. Further, the diameter of the wedge pin 220 is slightly greater than the radius of curvature of peripheral a groove which defines the neck 206, and the tip end of each of the wedge pins 220 is rounded.

A leaf spring 222 is further mounted to each of the chuck fingers 218, and the leaf spring 222 is disposed above the corresponding wedge pin 220. A distance corresponding to the height of the head 208 of the plug 202 is secured between the leaf spring 222 and the wedge pin 220.

The device 212 further includes a plug pusher 224. As is apparent from FIG. 22, the plug pusher 224 includes a vertically disposed air cylinder 226, and a plate 228 which is moved up and down by the operation of the air cylinder 226. A pusher 230 is mounted to the plate 228. The pusher 230 is located at the center between the pair of chuck fingers 218, and is projected downward from the plate 228. A coil spring is disposed between the pusher 230 and the plate 228 for biasing the pusher 230 downward.

Figure 22:
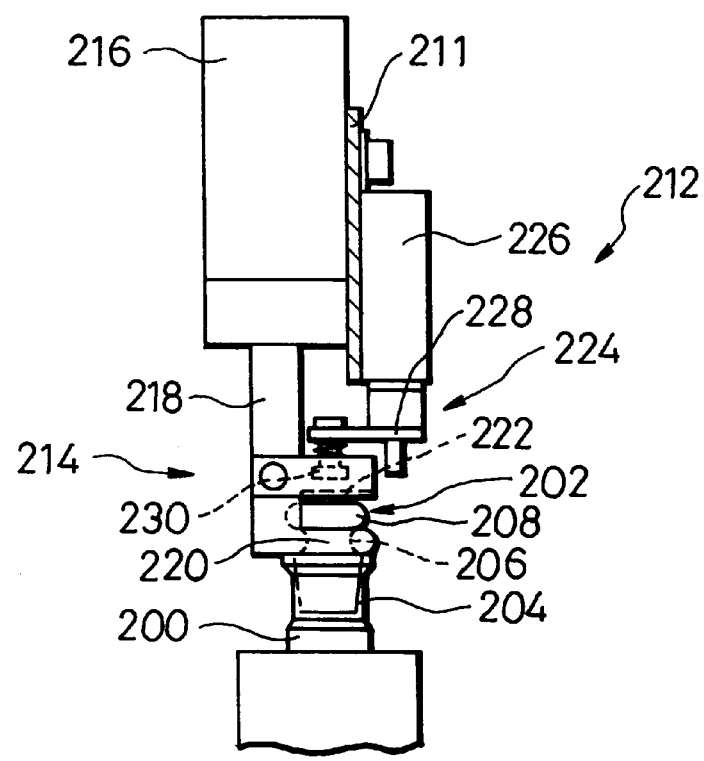
FIG. 22 is a side view of the plug opener device shown in FIG. 20.

As shown in FIGS. 20 and 22, the plug opener device 212 is moved such that the pair of wedge pins 220 are located at opposite sides of the plug 202 of the stoppered test tube 200. In this state, the chuck fingers 218 of the chuck 214 are closed, the pair of wedge pins 220 forcefully wedge between the head 208 of the plug 202 and the upper edge of the test tube 200 such as to sandwich the neck 206 of the plug 202 from both sides. As a result, even if the plug 202 clings on the opening of the test tube 200, the pair of wedge pins 220 can forcefully push out the plug 202 from the opening of the test tube 200. At this time, the head 208 of the plug 202 is sandwiched between the wedge pin 220 and the corresponding leaf spring 222 so that the plug 202 is prevented from popping out from the test tube 200. After that, the plug opener device 212 rises while holding the plug 202, and is moved to a predetermined standby position.

When the plug 202 is pulled out from the test tube 200 in this manner, the above described pouring process of solvent or the distribution process of solvent is carried out with respect to the test tube 200. Next, the plug opener device 212 moves from the standby position to the position above the test tube 200, and drops the plug 202 into the opening of the test tube 200. Thereafter, the plug pusher 224 lowers the pusher 230, the pusher 230 forcefully pushes the plug 202 into the opening of the test tube 200. According to the plug opener device 212, if the stopperd test tube 200 is used, the plug 202 thereof can reliably be opened and closed by the plug opener device 212.

Automatic Pretreatment System According to Third Embodiment

Any of the above described embodiments use the transfer path for transferring the tray or vial stand. However, such a transfer path is not necessarily required for carrying out the present invention. FIG. 23 shows an automatic pretreatment system according to a third embodiment. This pretreatment system similarly includes the first pouring section 91, the shaking section 42, the centrifuging section 136, the distribution section 92, the crystallizing section 158, the second pouring section 166 and the dissolving section 184. These sections are disposed in an arbitrary layout on the same floor surface for example.

The system of the third embodiment further includes a robot 238, a specimen storage section 230, a collecting section 232, a section 234 for supplying empty stoppered test tubes 200 and a specimen storage section 236. The robot 238 includes an access area covering all of the sections.

The specimen storage section 230 stores a large number of tube stands. The stoppered test tube is held in each of the tube stands of the section 230, and a specimen is previously accommodated in each of the stoppered test tubes. The collecting section 232 can receive the distribution processed test tubes together with the tube stand. Therefore, the sections 230 and 232 respectively correspond to the sending stocker 2 and the receiving stocker 4.

The supply section 234 also stores a large number of tube stands, and empty stoppered test tubes are held in the tube stands. The specimen liquid storage section 236 can receive a large number of tube stands, and these tube stands hold pretreated stoppered test tubes. Therefore, the sections 234 and 236 respectively correspond to the above described sending stocker 100 and the receiving stocker 102.

The robot 236 moves the tube stands between each of the sections. Each of the sections conducts a predetermined process for the received tube stand or test tubes. More specifically, the first pouring section 91, the distribution section 92 and the second pouring section 166 each includes the above described plug opener device 212.

The invention being thus described, it will be obvious that the same may be varied in many ways. Such variations are not to be regarded as a departure from the spirit and scope of the invention, and all such modifications as would be obvious to one skilled in the art are intended to be included within the scope of the following claims.

What is claimed is:

1. A system for carrying an automatic pretreatment prior to an analysis, comprising:
    a first storage section for storing first vessels, each of the first vessels having a cap or a plug and containing a specimen to be analyzed;
    a pouring section for pouring a solvent for preparing the specimen liquid in the first vessel, said pouring section including first opening/closing means for opening and closing the cap or plug of the first vessel;
    a shaking section for shaking the first vessel after the solvent is poured;
    a second storage section for storing empty second vessels, the second vessel having an open end;
    a distribution section for receiving the first vessel after said shaking process and at least one second vessel, and for distributing the specimen liquid in the first vessel to the second vessel, said distributing section including second opening/closing means for opening and closing the cap or plug of the first vessel;
    a closing section for closing the opening end of the second vessel after the specimen liquid is poured;
    a receiving section for receiving the second vessel from said closing section;
    first transfer means for sequentially transferring the first vessel from said first storage section to said pouring section and said shaking section, said first transfer means including a first transfer path for the first vessel; and
    second transfer means for transferring the second vessel from said second storage section to said receiving section via said distribution section and said closing section, said second transfer means including a second transfer path for the second vessel, and the first and second transfer paths being independent from each other.

2. The system according to claim 1, wherein
    the system further comprises a centrifuging section for receiving the first vessel by means of said first transfer means before the vessel is transferred from said shaking section to said distribution section, and centrifuging the specimen liquid in the first vessel, the specimen liquid in the first vessel is separated into a plurality of liquid layers by the centrifuging.

3. The system according to claim 2, wherein
    said distribution section further comprises a detector for detecting an interface between liquid layers in the specimen liquid in the first vessel.

4. The system according to claim 1, wherein
    the system further comprises a crystallizing section for receiving the second vessel from said distribution section by means of said second transfer means, and crystallizing the specimen liquid in the second vessel to a crystal, before the second vessel is transferred from said distribution section to said closing section.

5. The system according to claim 4, wherein
    the system further comprises a second pouring section for receiving the second vessel from said crystallizing section by means of said second transfer means, and pouring a second solvent into the second vessel, before the second vessel is transferred from said crystallizing section to said closing section.

6. The system according to claim 5, wherein
    the system further comprises a dissolving section for receiving the second vessel from said closing section by means of said second transfer means, and dissolving the crystal in the second vessel into the second solvent.

7. The system according to claim 2, wherein
    the system further comprises a crystallizing section for receiving the second vessel from said distribution section by means of said second transfer means, and crystallizing the specimen liquid in the second vessel to a crystal, before the second vessel is transferred from said distribution section to said closing section.

8. The system according to claim 7, wherein
    the system further comprises a second pouring section for receiving the second vessel from said crystallizing section by means of said second transfer means, and pouring a second solvent into the second vessel, before the second vessel is transferred from said distribution section to said closing section.

9. The system according to claim 8, wherein
    the system further comprises a dissolving section for receiving the second vessel from said closing section by means of said second transfer means, and dissolving the crystal in the second vessel into the second solvent.

10. The system according to claim 1, wherein
    the first and second vessels are transferred in a predetermined number in a state where the first and second vessels are held by corresponding holding members.

11. The system according to claim 10, wherein
    the system further comprises means for loading and unloading said holding member for the first vessels between said first transfer path and said shaking section.

12. The system according to claim 1, wherein
    the first vessel is a stoppered test tube including the plug, the plug being connected to a head through a neck, and
    said first and second opening/closing means includes a wedge member for wedging between the head of the plug and an opening edge of the test tube, and popping the plug out from the opening of the test tube.

* * * * *